(12) United States Patent
Swaile et al.

(10) Patent No.: US 10,076,490 B2
(45) Date of Patent: *Sep. 18, 2018

(54) AEROSOL ANTIPERSPIRANT COMPOSITIONS, PRODUCTS AND METHODS

(71) Applicant: The Procter & Gamble Company, Cincinnati, OH (US)

(72) Inventors: David Frederick Swaile, Cincinnati, OH (US); Rajeev Kumar Passi, West Chester, OH (US); Ann Christine Zoller, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/384,559

(22) Filed: Dec. 20, 2016

(65) Prior Publication Data
US 2017/0100325 A1    Apr. 13, 2017

Related U.S. Application Data

(63) Continuation of application No. 14/026,434, filed on Sep. 13, 2013, now Pat. No. 9,554,981.

(60) Provisional application No. 61/701,201, filed on Sep. 14, 2012.

(51) Int. Cl.
| | |
|---|---|
| A61K 8/891 | (2006.01) |
| A61Q 15/00 | (2006.01) |
| A61K 8/04 | (2006.01) |
| B65D 83/44 | (2006.01) |
| B65D 83/14 | (2006.01) |
| A61K 8/02 | (2006.01) |
| B65D 83/46 | (2006.01) |
| A61K 8/25 | (2006.01) |
| A61K 8/26 | (2006.01) |
| A61K 8/73 | (2006.01) |

(52) U.S. Cl.
CPC ............ *A61K 8/891* (2013.01); *A61K 8/0241* (2013.01); *A61K 8/046* (2013.01); *A61K 8/25* (2013.01); *A61K 8/26* (2013.01); *A61K 8/732* (2013.01); *A61Q 15/00* (2013.01); *B65D 83/44* (2013.01); *B65D 83/46* (2013.01); *B65D 83/752* (2013.01); *A61K 2800/34* (2013.01); *A61K 2800/87* (2013.01)

(58) Field of Classification Search
CPC ...... A61K 8/891; A61K 8/046; A61K 8/0241; A61K 2800/87; A61K 8/25; A61K 8/26; A61K 8/732; A61K 2800/34; A61Q 15/00; B65D 83/44; B65D 83/752; B65D 83/46

See application file for complete search history.

(56) References Cited

U.S. PATENT DOCUMENTS

| | | |
|---|---|---|
| 2,890,817 A | 6/1959 | Rheinstrom |
| 4,383,988 A | 5/1983 | Teng et al. |
| 4,396,152 A | 8/1983 | Abplanalp |
| 4,605,553 A | 8/1986 | Passalacqua |
| 4,724,139 A | 2/1988 | Palinczar |
| 4,806,338 A | 2/1989 | Smith |
| 4,822,603 A | 4/1989 | Farris et al. |
| 4,840,789 A | 6/1989 | Orr et al. |
| 4,853,214 A | 8/1989 | Orr |
| 4,863,721 A | 9/1989 | Beck et al. |
| 4,889,711 A | 12/1989 | Kai et al. |
| 4,985,238 A | 1/1991 | Tanner et al. |
| 5,019,375 A | 5/1991 | Tanner et al. |
| 5,069,897 A | 12/1991 | Orr |
| 5,082,652 A | 1/1992 | Mayfield et al. |
| 5,169,626 A | 12/1992 | Tanner et al. |
| 5,176,903 A | 1/1993 | Goldberg et al. |
| 5,178,881 A | 1/1993 | Mackles et al. |
| 5,294,447 A | 3/1994 | Mackles et al. |
| 5,298,236 A | 3/1994 | Orr et al. |
| 5,378,452 A | 1/1995 | Greczyn |

(Continued)

FOREIGN PATENT DOCUMENTS

| | | |
|---|---|---|
| AU | 2007100166 A4 | 3/2007 |
| DE | 4439443 | 5/1996 |

(Continued)

OTHER PUBLICATIONS

International Search Report and Written Opinion of the International Searching Authority, Application No. PCT/US2013/059685, dated Nov. 17, 2014, 12 pages.
All Office Actions, U.S. Appl. No. 14/026,434.
All Office Actions, U.S. Appl. No. 14/307,433.
All Office Actions, U.S. Appl. No. 14/307,457.
All Office Actions, U.S. Appl. No. 14/307,462.
All Office Actions, U.S. Appl. No. 14/307,466.
All Office Actions, U.S. Appl. No. 14/307,438.

(Continued)

*Primary Examiner* — Sean M Basquill
(74) *Attorney, Agent, or Firm* — Kathleen Y. Carter; Betty J. Zea

(57) ABSTRACT

An aerosol antiperspirant composition is provided. The aerosol antiperspirant composition includes a propellant having a concentration from 30% to 65% by weight and an antiperspirant composition. The antiperspirant composition includes one or more liquid materials, wherein the one or more liquid materials comprise one or more non-volatile silicone fluids having a concentration from 40% to about 70% by weight; antiperspirant active particulates; one or more non-antiperspirant active particulates that are substantially inert; and wherein the antiperspirant composition has a total particulate concentration from 30% to about 60% by weight and the antiperspirant composition has a viscosity greater than 1,000 centipoise.

20 Claims, 13 Drawing Sheets

(56) References Cited

U.S. PATENT DOCUMENTS

| | | |
|---|---|---|
| 5,400,920 A | 3/1995 | Barnhart |
| 5,417,357 A | 5/1995 | Yquel |
| 5,417,964 A | 5/1995 | Carlson, Sr. et al. |
| 5,444,096 A | 8/1995 | McCrea et al. |
| 5,449,511 A | 9/1995 | Coe |
| 5,593,069 A | 1/1997 | Jinks |
| 5,605,682 A | 2/1997 | Ross et al. |
| 5,609,300 A | 3/1997 | Conatser |
| 5,623,920 A | 4/1997 | Bryant |
| 5,628,989 A | 5/1997 | Harashima et al. |
| 5,628,990 A | 5/1997 | Murphy et al. |
| 5,639,219 A | 6/1997 | Conatser |
| 5,657,790 A | 8/1997 | Mohn |
| 5,690,256 A | 11/1997 | Smith |
| 5,697,532 A | 12/1997 | Wilde et al. |
| 5,718,890 A | 2/1998 | Putnam et al. |
| 5,735,465 A | 4/1998 | Laforcade |
| 5,750,096 A | 5/1998 | Guskey |
| 5,756,082 A | 5/1998 | Cashin et al. |
| 5,770,187 A | 6/1998 | Hasebe et al. |
| 5,772,085 A | 6/1998 | Bryant et al. |
| 5,785,301 A | 7/1998 | Scheindel |
| 5,794,660 A | 8/1998 | Mohn |
| 5,803,319 A | 9/1998 | Smith et al. |
| 5,833,964 A | 11/1998 | Linn et al. |
| 5,840,286 A | 11/1998 | Gardlik et al. |
| 5,840,287 A | 11/1998 | Guskey et al. |
| 5,840,288 A | 11/1998 | Guskey et al. |
| 5,840,289 A | 11/1998 | Hall |
| 5,843,414 A | 12/1998 | Hilvert et al. |
| 5,846,520 A | 12/1998 | Guskey et al. |
| 5,849,276 A | 12/1998 | Guskey et al. |
| 5,871,717 A | 2/1999 | Bretzler et al. |
| 5,891,424 A | 4/1999 | Bretzler et al. |
| 5,891,425 A | 4/1999 | Bretzler et al. |
| 5,895,644 A | 4/1999 | Albanese et al. |
| 5,902,570 A | 5/1999 | Bretzler et al. |
| 5,906,046 A | 5/1999 | Abplanalp et al. |
| 5,921,439 A | 7/1999 | Losenno et al. |
| 5,927,563 A | 7/1999 | Kellner |
| 5,932,199 A | 8/1999 | Esser |
| 5,939,056 A | 8/1999 | Fletcher et al. |
| 5,941,424 A | 8/1999 | Hildebrandt |
| 5,945,085 A | 8/1999 | Salas et al. |
| 5,957,333 A | 9/1999 | Losenno et al. |
| 5,957,342 A | 9/1999 | Gallien |
| 5,967,382 A | 10/1999 | Lasserre et al. |
| 5,972,319 A | 10/1999 | Linn et al. |
| 5,985,252 A | 11/1999 | Hall et al. |
| 6,006,954 A | 12/1999 | Warby |
| 6,039,306 A | 3/2000 | Pericard et al. |
| 6,045,784 A | 4/2000 | Ruebusch et al. |
| 6,048,518 A | 4/2000 | Bianchi et al. |
| 6,070,770 A | 6/2000 | Tada et al. |
| 6,083,492 A | 7/2000 | Modi |
| 6,092,698 A | 7/2000 | Bayer |
| 6,110,449 A | 8/2000 | Bacon et al. |
| 6,112,945 A | 9/2000 | Woods |
| 6,112,950 A | 9/2000 | Di Giovanni et al. |
| 6,113,070 A | 9/2000 | Holzboog |
| 6,123,932 A | 9/2000 | Guskey et al. |
| 6,132,744 A | 10/2000 | Chehab et al. |
| 6,136,302 A | 10/2000 | Juneja et al. |
| 6,136,303 A | 10/2000 | Ruebusch et al. |
| 6,145,712 A | 11/2000 | Benoist |
| 6,171,601 B1 | 1/2001 | Gardlik et al. |
| 6,187,300 B1 | 2/2001 | Motley et al. |
| 6,187,301 B1 | 2/2001 | Scavone et al. |
| 6,197,286 B1 | 3/2001 | Scavone et al. |
| 6,231,841 B1 | 5/2001 | Franklin et al. |
| 6,245,234 B1 | 6/2001 | Hough et al. |
| 6,261,543 B1 | 7/2001 | Fletcher et al. |
| 6,296,155 B1 | 10/2001 | Smith |
| 6,299,024 B1 | 10/2001 | Corba |
| 6,318,603 B1 | 11/2001 | Burt |
| 6,342,210 B1 | 1/2002 | Cai et al. |
| 6,352,688 B1 | 3/2002 | Scavone et al. |
| 6,357,633 B1 | 3/2002 | Zimmerhackel et al. |
| 6,361,765 B1 | 3/2002 | Emslie et al. |
| 6,361,766 B1 | 3/2002 | Franklin et al. |
| 6,375,036 B1 | 4/2002 | Woods |
| 6,375,378 B1 | 4/2002 | Kitaura |
| 6,375,938 B1 | 4/2002 | Clothier, Jr. et al. |
| 6,382,474 B1 | 5/2002 | Woods et al. |
| 6,383,476 B1 | 5/2002 | Scavone et al. |
| 6,387,356 B1 | 5/2002 | Csernica et al. |
| 6,387,358 B2 | 5/2002 | Chuah et al. |
| 6,394,364 B1 | 5/2002 | Abplanalp |
| 6,403,067 B1 | 6/2002 | Schamper et al. |
| 6,403,072 B1 | 6/2002 | Scavone et al. |
| 6,416,750 B1 | 7/2002 | Harper et al. |
| 6,418,920 B1 | 7/2002 | Marr |
| 6,425,503 B1 | 7/2002 | Scheindel |
| 6,426,062 B1 | 7/2002 | Chopra et al. |
| 6,428,777 B1 | 8/2002 | Boyle et al. |
| 6,431,413 B2 | 8/2002 | Corba |
| 6,436,382 B1 | 8/2002 | Chopra et al. |
| 6,454,140 B1 | 9/2002 | Jinks |
| 6,468,511 B1 | 10/2002 | Chopra et al. |
| 6,488,919 B1 | 12/2002 | Murphy et al. |
| 6,510,969 B2 | 1/2003 | Di Giovanni et al. |
| 6,534,046 B1 | 3/2003 | Golz-Berner et al. |
| 6,555,098 B1 | 4/2003 | Murphy et al. |
| 6,588,627 B2 | 7/2003 | Petterson et al. |
| 6,588,628 B2 | 7/2003 | Abplanalp et al. |
| 6,588,631 B2 | 7/2003 | Sanchez |
| RE38,207 E | 8/2003 | Benoist |
| 6,607,106 B2 | 8/2003 | Henry et al. |
| 6,610,279 B2 | 8/2003 | Chopra et al. |
| 6,619,515 B1 | 9/2003 | Abplanalp et al. |
| 6,640,805 B2 | 11/2003 | Castro et al. |
| 6,644,306 B1 | 11/2003 | Riebe et al. |
| 6,645,475 B2 | 11/2003 | Franklin et al. |
| 6,652,843 B2 | 11/2003 | Fairclough et al. |
| 6,703,005 B2 | 3/2004 | Allan et al. |
| 6,719,965 B2 | 4/2004 | Tomczak |
| 6,726,901 B2 | 4/2004 | Yin et al. |
| 6,749,841 B2 | 6/2004 | Joshi et al. |
| 6,793,915 B1 | 9/2004 | Guenin et al. |
| 6,805,855 B2 | 10/2004 | Mattai et al. |
| 6,849,251 B2 | 2/2005 | Banowski et al. |
| 6,978,196 B2 | 12/2005 | Albertus |
| 6,978,915 B1 | 12/2005 | Russell |
| 6,978,916 B2 | 12/2005 | Smith |
| 6,986,885 B2 | 1/2006 | Mattai et al. |
| 6,994,845 B2 | 2/2006 | Mattai et al. |
| 7,033,579 B1 | 4/2006 | Scavone |
| 7,086,571 B2 | 8/2006 | Warby et al. |
| 7,128,901 B2 | 10/2006 | Jonas et al. |
| 7,235,261 B2 | 6/2007 | Smith et al. |
| 7,261,225 B2 | 8/2007 | Rueschhoff et al. |
| 7,278,556 B2 | 10/2007 | Goujon et al. |
| 7,329,403 B2 | 2/2008 | Chuah et al. |
| 7,341,169 B2 | 3/2008 | Bayer |
| 7,341,984 B2 | 3/2008 | Wilson et al. |
| 7,364,055 B2 | 4/2008 | Yquel et al. |
| 7,404,946 B2 | 7/2008 | Bowens-Jones et al. |
| 7,465,698 B2 | 12/2008 | Wilson et al. |
| 7,479,477 B2 | 1/2009 | Wilson et al. |
| 7,501,136 B2 | 3/2009 | Hagura et al. |
| 7,563,384 B2 | 7/2009 | Thomas et al. |
| 7,597,818 B2 | 10/2009 | Singh et al. |
| 7,605,117 B2 | 10/2009 | Wilson et al. |
| 7,622,435 B2 | 11/2009 | Wilson et al. |
| 7,735,696 B2 | 6/2010 | Allsop |
| 7,744,857 B2 | 6/2010 | Beachy et al. |
| 7,766,030 B2 | 8/2010 | Askew |
| 7,790,202 B1 | 9/2010 | Martell |
| 7,793,805 B2 | 9/2010 | Allsop |
| 7,793,806 B2 | 9/2010 | Allsop |
| 7,799,318 B2 | 9/2010 | Esposito et al. |
| 7,833,433 B2 | 11/2010 | Singh et al. |
| 7,959,041 B2 | 6/2011 | Miller et al. |
| 7,997,458 B2 | 8/2011 | Wickham |

(56) References Cited

U.S. PATENT DOCUMENTS

| | | | |
|---|---|---|---|
| 7,997,459 B2 | 8/2011 | Warby | |
| 8,002,247 B2 | 8/2011 | Birtcher et al. | |
| 8,008,244 B2 | 8/2011 | Knopeck et al. | |
| 8,075,796 B2 | 12/2011 | Rao et al. | |
| 8,097,181 B2 | 1/2012 | Leck et al. | |
| 8,101,094 B2 | 1/2012 | Howell et al. | |
| 8,114,828 B2 | 2/2012 | Bowman et al. | |
| 8,133,407 B2 | 3/2012 | Zyhowski et al. | |
| 8,147,709 B2 | 4/2012 | Mahler et al. | |
| 8,148,317 B2 | 4/2012 | Singh et al. | |
| 8,210,400 B2 | 7/2012 | Scheindel | |
| 8,257,689 B2 | 9/2012 | Pan | |
| 8,333,902 B2 | 12/2012 | Mahler et al. | |
| 8,349,339 B2 | 1/2013 | Cropper et al. | |
| 8,388,857 B2 | 3/2013 | Elsheikh et al. | |
| 8,393,554 B2 | 3/2013 | Yamamoto et al. | |
| 8,394,286 B2 | 3/2013 | Leck et al. | |
| 8,399,713 B2 | 3/2013 | Bartelt et al. | |
| 8,444,874 B2 | 5/2013 | Singh et al. | |
| 8,496,846 B2 | 7/2013 | Rao et al. | |
| 8,518,384 B2 | 8/2013 | Fletcher et al. | |
| 8,529,786 B2 | 9/2013 | Leck et al. | |
| 8,535,555 B2 | 9/2013 | Feiring et al. | |
| 8,557,260 B2 | 10/2013 | Falk | |
| 8,590,755 B2 | 11/2013 | Davideit et al. | |
| 8,596,557 B2 | 12/2013 | Yamamoto et al. | |
| 8,597,622 B2 | 12/2013 | Lemoine et al. | |
| 8,628,681 B2 | 1/2014 | Low | |
| 8,637,443 B2 | 1/2014 | Basu et al. | |
| 8,663,494 B2 | 3/2014 | Howell et al. | |
| 9,554,981 B2* | 1/2017 | Swaile | A61K 8/0241 |
| 9,554,982 B2* | 1/2017 | Swaile | A61K 8/0241 |
| 2002/0034481 A1 | 3/2002 | Bianchi et al. | |
| 2002/0039563 A1 | 4/2002 | Franklin et al. | |
| 2002/0079337 A1 | 6/2002 | Jinks | |
| 2002/0164296 A1 | 11/2002 | Schamper et al. | |
| 2002/0190085 A1 | 12/2002 | Stanford | |
| 2003/0010794 A1 | 1/2003 | Herdtle et al. | |
| 2003/0024953 A1 | 2/2003 | Lilienthal | |
| 2003/0053970 A1 | 3/2003 | Bruening et al. | |
| 2003/0071080 A1 | 4/2003 | Yquel | |
| 2003/0113282 A1 | 6/2003 | Buranachokpaisan | |
| 2003/0161800 A1 | 8/2003 | Guenin et al. | |
| 2003/0235545 A1 | 12/2003 | Guenin et al. | |
| 2003/0235546 A1 | 12/2003 | Mattai et al. | |
| 2004/0141934 A1 | 7/2004 | Fei et al. | |
| 2004/0202630 A1 | 10/2004 | Joshi et al. | |
| 2004/0213748 A1 | 10/2004 | Chuah et al. | |
| 2004/0222244 A1 | 11/2004 | Groeger | |
| 2004/0241123 A1 | 12/2004 | Popoff et al. | |
| 2004/0265254 A1 | 12/2004 | Tomczak | |
| 2005/0084510 A1 | 4/2005 | Carson | |
| 2005/0169851 A1 | 8/2005 | Smith | |
| 2005/0191257 A1 | 9/2005 | Brahms et al. | |
| 2005/0281767 A1 | 12/2005 | Walling et al. | |
| 2006/0029624 A1 | 2/2006 | Banowski et al. | |
| 2006/0033072 A1 | 2/2006 | Wilson et al. | |
| 2006/0039877 A1 | 2/2006 | Mattai et al. | |
| 2006/0104918 A1* | 5/2006 | Brown | A61K 8/046 424/47 |
| 2006/0210502 A1 | 9/2006 | Galante et al. | |
| 2006/0263311 A1 | 11/2006 | Scavone et al. | |
| 2006/0263312 A1 | 11/2006 | Scavone et al. | |
| 2006/0269484 A1 | 11/2006 | Knopeck et al. | |
| 2007/0003499 A1 | 1/2007 | Shen et al. | |
| 2007/0036738 A1* | 2/2007 | Fletcher | A61K 8/046 424/65 |
| 2007/0092463 A1 | 4/2007 | Kim et al. | |
| 2007/0098646 A1 | 5/2007 | Nappa et al. | |
| 2007/0248551 A1 | 10/2007 | Lemoine et al. | |
| 2007/0292460 A1 | 12/2007 | Schiemann et al. | |
| 2008/0098600 A1 | 5/2008 | Riebe et al. | |
| 2008/0121666 A1 | 5/2008 | Purkins | |
| 2008/0157022 A1 | 7/2008 | Singh et al. | |
| 2008/0166305 A1 | 7/2008 | Singh et al. | |
| 2008/0171652 A1 | 7/2008 | Singh et al. | |
| 2008/0187504 A1 | 8/2008 | Fan et al. | |
| 2008/0187562 A1 | 8/2008 | Fan et al. | |
| 2008/0190418 A1 | 8/2008 | Miller et al. | |
| 2008/0213322 A1 | 9/2008 | Birman et al. | |
| 2008/0224082 A1 | 9/2008 | Warby | |
| 2008/0230566 A1 | 9/2008 | Frutin | |
| 2008/0233067 A1 | 9/2008 | Lee et al. | |
| 2008/0292564 A1 | 11/2008 | Singh et al. | |
| 2008/0317694 A1 | 12/2008 | Bruening et al. | |
| 2009/0047226 A1 | 2/2009 | Teckenbrock et al. | |
| 2009/0078902 A1 | 3/2009 | Flynn | |
| 2009/0087396 A1 | 4/2009 | Hwang et al. | |
| 2009/0117066 A1 | 5/2009 | Massaro et al. | |
| 2009/0145932 A1 | 6/2009 | Davideit et al. | |
| 2009/0220555 A1 | 9/2009 | Hwang et al. | |
| 2009/0253612 A1* | 10/2009 | Mushock | A23L 2/39 512/4 |
| 2009/0304617 A1 | 12/2009 | Banowski et al. | |
| 2009/0317345 A1 | 12/2009 | Joshi et al. | |
| 2010/0044400 A1 | 2/2010 | Laidler | |
| 2010/0051651 A1 | 3/2010 | Allsop | |
| 2010/0104612 A1 | 4/2010 | Cropper et al. | |
| 2010/0104613 A1 | 4/2010 | Chan et al. | |
| 2010/0112022 A1 | 5/2010 | Hoying et al. | |
| 2010/0122545 A1 | 5/2010 | Minor et al. | |
| 2010/0200799 A1 | 8/2010 | Mouli | |
| 2010/0224656 A1 | 9/2010 | Scheindel | |
| 2010/0260698 A1 | 10/2010 | Galante et al. | |
| 2011/0005723 A1 | 1/2011 | Mouli | |
| 2011/0031436 A1 | 2/2011 | Mahler et al. | |
| 2011/0232939 A1 | 9/2011 | Luly et al. | |
| 2011/0253927 A1 | 10/2011 | Minor et al. | |
| 2011/0257282 A1 | 10/2011 | Alexander | |
| 2011/0275723 A1 | 11/2011 | Hulse et al. | |
| 2012/0003284 A1 | 1/2012 | Arnaud et al. | |
| 2012/0074349 A1 | 3/2012 | Leck et al. | |
| 2012/0076839 A1 | 3/2012 | Chan et al. | |
| 2012/0107261 A1 | 5/2012 | Banowski et al. | |
| 2012/0126187 A1 | 5/2012 | Low | |
| 2012/0138639 A1 | 6/2012 | Scheindel | |
| 2012/0141385 A1 | 6/2012 | Bowman et al. | |
| 2012/0168663 A1 | 7/2012 | Singh et al. | |
| 2012/0177589 A1 | 7/2012 | Banowski et al. | |
| 2012/0187330 A1 | 7/2012 | Singh et al. | |
| 2012/0305480 A1 | 12/2012 | Low | |
| 2012/0305830 A1 | 12/2012 | Low | |
| 2012/0318828 A1 | 12/2012 | Nappa et al. | |
| 2013/0032751 A1 | 2/2013 | Low | |
| 2013/0161554 A1 | 6/2013 | Elsheikh et al. | |
| 2013/0187078 A1 | 7/2013 | Low | |
| 2013/0193368 A1 | 8/2013 | Low | |
| 2013/0221262 A1 | 8/2013 | Minor et al. | |
| 2013/0283834 A1 | 10/2013 | Rao et al. | |
| 2014/0020416 A1 | 1/2014 | Feiring et al. | |
| 2014/0048568 A1 | 2/2014 | Demey et al. | |
| 2017/0100324 A1* | 4/2017 | Swaile | A61K 8/891 |

FOREIGN PATENT DOCUMENTS

| | | |
|---|---|---|
| DE | 19860969 | 3/2006 |
| EP | 0272919 B1 | 4/1992 |
| EP | 0684038 A2 | 11/1995 |
| EP | 1095959 A2 | 5/2001 |
| EP | 0674899 B1 | 8/2001 |
| EP | 1183003 | 3/2002 |
| EP | 1244423 | 10/2002 |
| EP | 1535860 | 6/2005 |
| EP | 1563829 | 8/2005 |
| EP | 1377268 B1 | 8/2007 |
| EP | 2 301 516 A2 | 3/2011 |
| EP | 2349185 | 8/2011 |
| EP | 1858485 B1 | 9/2013 |
| FR | 2705323 | 11/1994 |
| FR | 2814727 | 4/2002 |
| FR | 2842180 | 1/2004 |
| GB | 2296189 A | 6/1996 |
| GB | 2322847 A | 9/1998 |
| GB | 2323351 A | 9/1998 |

(56) References Cited

FOREIGN PATENT DOCUMENTS

| | | |
|---|---|---|
| GB | 2430188 A | 3/2007 |
| GB | 2440258 A | 1/2008 |
| GB | 2456028 | 7/2009 |
| GB | 2477865 A | 8/2011 |
| JP | 08-040474 | 2/1996 |
| JP | 2000-219505 | 8/2000 |
| JP | 2001-220135 | 8/2001 |
| JP | 2004-215425 | 7/2004 |
| JP | 2004-315425 A | 11/2004 |
| JP | 2006-001763 | 1/2006 |
| JP | 2006-111350 | 4/2006 |
| JP | 2006-232674 | 9/2006 |
| JP | 2009-102271 | 5/2009 |
| JP | 2010-208675 | 9/2010 |
| JP | 2011-126862 | 6/2011 |
| JP | 2011-184585 | 9/2011 |
| WO | 94/24995 A1 | 11/1994 |
| WO | 96/04884 A1 | 2/1996 |
| WO | 97/16161 | 5/1997 |
| WO | 97/16162 | 5/1997 |
| WO | 99/50156 A1 | 10/1999 |
| WO | 00/44339 A1 | 8/2000 |
| WO | 2001/47476 | 7/2001 |
| WO | 02/069924 A1 | 9/2002 |
| WO | 2003/92642 | 11/2003 |
| WO | 2004/039344 A1 | 5/2004 |
| WO | 2008/025524 A2 | 3/2008 |
| WO | 2008/027512 A2 | 3/2008 |
| WO | 2008/027513 A2 | 3/2008 |
| WO | 2008/027516 A1 | 3/2008 |
| WO | 2008/027595 A1 | 3/2008 |
| WO | 2009/039565 A1 | 4/2009 |
| WO | 2009/101000 | 8/2009 |
| WO | 2010/009977 A2 | 1/2010 |
| WO | 2010-35701 | 4/2010 |
| WO | 2010/089314 A1 | 8/2010 |
| WO | 2010/145919 A2 | 12/2010 |
| WO | 2010/145921 | 12/2010 |
| WO | 2012/10684 | 1/2012 |
| WO | 2012/024290 A1 | 2/2012 |
| WO | 2012/085055 A22 | 6/2012 |

OTHER PUBLICATIONS

All Office Actions, U.S. Appl. No. 14/307,447.
All Office Actions, U.S. Appl. No. 14/307,455.
All Office Actions, U.S. Appl. No. 14/656,118.
All Office Actions, U.S. Appl. No. 14/656,144.
PCT International Search Report and Written Opinion for PCT/US2013/068982, dated Mar. 14, 2014.

* cited by examiner

… (1)

AEROSOL ANTIPERSPIRANT COMPOSITIONS, PRODUCTS AND METHODS

TECHNICAL FIELD

One aspect of the invention relates generally to antiperspirant compositions. Another aspect of the invention relates generally to spray devices containing an antiperspirant composition and a propellant. Yet another aspect of the invention relates generally to methods of using antiperspirant spray devices.

BACKGROUND

Body odor may be generated in the area under the arms due to a high concentration of sweat glands. While perspiration is odorless, it contains natural oils that can be nutrient source for bacteria living on the skin. These bacteria interact with the natural oils, converting them into odor producing compounds. Antiperspirant compositions contain an active, such as an aluminum salt, that reacts with the electrolytes in perspiration to form a plug in the ducts of sweat glands. The plugs prevent perspiration from exiting the duct, thereby depriving the the bacteria of water and a food source. Antiperspirant compositions may be applied to the skin in either a contact type product form, e.g., a stick or roll-on, or non-contact type product form, such as an aerosol spray. Aerosol spray devices that dispense an antiperspirant composition are known in the art. Various examples are described in U.S. Pat. Nos. 4,152,416; 4,806,338; 4,840, 786; 4,904,463; 4,935,224; 5,298,236; 5,605,682; 5,814, 309; 7,815,899; EP 674,899; WO 96/04884; WO 2004/ 014330; and WO 2007/001842.

Many aerosol antiperspirant users desire a product that minimizes the appearance of residue on the skin, has a dry rather than wet feel, has rapid perceived drying, is not sticky, provides a cool/fresh feeling at time of application, provides long lasting wetness and/or odor protection, is provided in a form factor that is easily portable in purses or small bags (as some users may apply the antiperspirant composition more than once a day) and minimizes the gassy cloud that forms during dispensing. While the relative importance/desirability of these characteristics may vary by geographical region and gender and not all users desire all or the same set of characteristics, there appears to be a generally universal desire among aerosol antiperspirant users for one or more of a dry rather than wet feel, minimizing the appearance of residue, and providing long lasting wetness/odor protection or efficacy.

While some currently marketed aerosol spray devices may provide at least some of these characteristics to varying degrees, there are often tradeoffs involved. For example, some currently available aerosol antiperspirant spray devices have relatively high propellant concentrations (e.g., greater than 75% and often greater than 80%). A high propellant concentration dilutes the antiperspirant composition, which in turn may help reduce the risk of clogging within the spray device. However, a high propellant concentration may also produce a large volume of gas upon exiting the spray device resulting in a gassy cloud and/or a turbulent spray. Deposition efficiency (e.g., the amount of antiperspirant active and/or fragrance deposited on skin compared to the amount dispensed) may in turn be reduced due to the large amount of antiperspirant active and/or fragrance lost to the environment via the gassy cloud rather than deposited on the skin. In addition, these spray devices are typically large (greater than 150 ml) in order to accommodate the high propellant concentration and large amount of antiperspirant composition, resulting in spray devices that may be more difficult to carry in small purses and the like. A high propellant concentration may also result in solubilization of liquid fragrance materials into the propellant during storage, resulting in more of the liquid fragrance material being lost to the environment with the propellant rather than deposited on the skin. Many currently available aerosol antiperspirant compositions also incorporate a volatile liquid (e.g., cyclopentasiloxane) as a carrier for the antiperspirant active. The volatile liquid evaporates following application to the skin, resulting in a dry skin feel, but sometimes leaves behind a visible residue (the antiperspirant active) that is subject to flaking and/or transfer to clothing. Flaking (or transfer) of the antiperspirant active may also reduce antiperspirant efficacy. Therefore, there is continuing desire to provide improved aerosol antiperspirant compositions and products.

SUMMARY OF THE DISCLOSURE

In one aspect, an aerosol antiperspirant composition is provided. The aerosol antiperspirant composition includes a propellant having a concentration from 30% to 65% by weight and an antiperspirant composition. The antiperspirant composition includes one or more liquid materials, wherein the one or more liquid materials comprise one or more non-volatile silicone fluids having a concentration from 40% to about 70% by weight; antiperspirant active particulates; one or more non-antiperspirant active particulates that are substantially inert; and wherein the antiperspirant composition has a total particulate concentration from 30% to about 60% by weight and the antiperspirant composition has a viscosity greater than 1,000 centipoise.

BRIEF DESCRIPTION OF THE DRAWINGS

While the specification concludes with claims, it is believed that the same will be better understood from the following description taken in conjunction with the accompanying drawings wherein like numbers illustrate like elements throughout the views and in which:

DETAILED DESCRIPTION

A spray device, container, composition, propellant, etc. may comprise, consist essentially of, or consist of, various combinations of the materials, features, structures, and/or characteristics described herein.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the antiperspirant composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. The term "molecular weight" or "M.Wt." as used herein refers to the number average molecular weight unless otherwise stated.

The term "antiperspirant composition" refers to any composition containing an antiperspirant active and which is intended to be sprayed onto skin, exclusive of a propellant.

The term "antiperspirant efficacy" refers to the amount of wetness protection provided by application of an antiperspirant composition to an underarm area (or axillia) by a spray device. Antiperspirant efficacy may be quantified by the amount (mg) of sweat collected following exposure to a hot room compared to a baseline amount.

The term "bulking or suspending material" refers to a material which is intended to reduce settling of a particulate from a liquid and/or reduce the severity of particulate caking post settling.

The term "clogging" refers to: i) either a blocked passage, orifice, hole or other opening resulting in little or no mass flow out of a container when the actuator is activated, or ii) a valve stuck at least partially open from accumulated composition, resulting in semi-continuous or continuous leakage of the antiperspirant composition and/or a propellant from the spray device, or iii) accumulation of antiperspirant composition within a portion of the flow path of the container which substantially impacts performance of the spray device.

The term "deposition efficiency" refers to the percentage of a material (e.g., antiperspirant active, fragrance material, antiperspirant composition, etc.) that is deposited on a target surface compared to the amount of material that exits a spray device.

The term "particulate", as used herein, refers to a material that is solid or hollow or porous (or a combination thereof) and which is substantially or completely insoluble in the liquid materials of an antiperspirant composition.

The term "propellant" refers to one or more gases that are used to pressurize the antiperspirant composition to facilitate egress of the antiperspirant composition from the container. Some propellants may be a mixture of gases (e.g., A-46 which may be a mixture of isobutane, butane and propane). A propellant may be in the form of a liquid (i.e., a liquefied gas) when under pressure within the reservoir of a spray device. In addition, a propellant may be in its gaseous state within the head space of the reservoir. A propellant may be present in both a liquefied form and its gaseous state within the reservoir. Unless specified otherwise (e.g., liquid propellant or gaseous propellant), the term propellant is intended to encompass the liquefied form and the gaseous state individually and collectively.

The term "substantially free of" refers to an amount of a material that is less than 1%, 0.5%, 0.25%, 0.1%, 0.05%, 0.01%, or 0.001% by weight of an antiperspirant composition. "Free of" refers to no detectable amount of the stated ingredient or thing.

The term "total fill" refers to the total amount of materials added to or stored within a reservoir(s) of a container. For example, total fill includes the propellant and antiperspirant composition stored within a spray device after completion of filling and prior to first use.

The term "viscosity" means dynamic viscosity (measured in centipoise, cPs, or Pascal-second, Pa·s) or kinematic viscosity (measured in centistokes, cSt, or $m^2/s$) of a liquid at approximately 25° C. and ambient conditions. Dynamic viscosity may be measured using a rotational viscometer, such as a Brookfield Dial Reading Viscometer Model 1-2 RVT available from Brookfield Engineering Laboratories (USA) or other substitutable model as known in the art. Typical Brookfield spindles which may be used include, without limitation, RV-7 at a spindle speed of 20 rpm, recognizing that the exact spindle may be selected as needed by one skilled in the art. Kinematic viscosity may be determined by dividing dynamic viscosity by the density of the liquid (at 25° C. and ambient conditions), as known in the art.

I. Propellants

A spray device comprises a propellant stored in one or more reservoirs of the container. The propellant may be stored in the same reservoir as an antiperspirant composition or a separate reservoir, although it is preferred that the propellant is stored within the same reservoir as the antiperspirant composition. The propellant may be present in a liquefied form that is miscible with liquid carriers of the antiperspirant composition as well as gaseous state within a head space of the reservoir. The liquid propellant and the antiperspirant composition form a mixture that travels through the container, eventually exiting the container where the liquid propellant vaporizes to form a spray.

Propellant concentration is one of many design variables that may affect performance of an antiperspirant spray device. For example, propellant concentration may impact the mass flow of the antiperspirant composition. The antiperspirant composition mass flow refers to that portion of the total mass flow of the liquid propellant/antiperspirant composition mixture that is attributable to the antiperspirant composition. As propellant concentration decreases, the density of the liquid propellant/antiperspirant composition mixture increases. Said another way, the antiperspirant composition is less diluted by the liquid propellant. As a consequence, the ratio of antiperspirant composition to liquid propellant in the total mass flow of the mixture increases with decreasing propellant concentration. This effect is most pronounced for hydrocarbon propellants (e.g., butane, isobutene, propane, etc.), which may have a density below that of the antiperspirant composition resulting in a larger volume fraction of the total mass flow. Decreasing propellant concentration may improve antiperspirant efficacy by: 1) increasing antiperspirant composition mass flow (and hence the amount of antiperspirant active deposited on skin per use), and ii) reducing the amount of antiperspirant composition lost to the environment in the form of a gassy cloud (due to less liquid propellant vaporizing and/or a less turbulent spray).

Propellant concentration may also affect the amount of fragrance deposited on skin. Many liquid fragrance materials are soluble in common propellants. As propellant concentration decreases, less of the liquid fragrance material may solubilize in the propellant during storage. Less solubilization may mean less of the fragrance material is lost to the environment as the liquid propellant turns to gas, and therefore more liquid fragrance material may be deposited on the skin as part of the antiperspirant composition. This effect may be seen in FIG. 1, which is a graph of the amount of fragrance deposited on a blotter card for various propellant concentrations (e.g., 84%, 65%, and 50%) and different propellants (e.g., A-46, A-31, and A-17, each propellant having a different equilibrium vapor pressure). The antiperspirant composition comprised dimethicone and a liquid fragrance material comprising known fragrance accords (at a total concentration of approximately 5.5% by weight of the antiperspirant composition). The antiperspirant composition was sprayed onto commercially available aerosol perfume blotter cards for a period of three seconds from a distance of approximately 152 mm (6 inches). The total weight dispensed was determined by weighing both the spray device and the blotter cards before and after dispensing. The blotter cards were then individually placed in 125 ml I-chem jars, and the perfume accords were extracted using hexane followed by analysis via liquid injection gas chromatography with mass spectrometric detection to determine the total amount of fragrance deposited, represented in FIG. 1 along the y-axis as the percent deposited.

Figure 1:
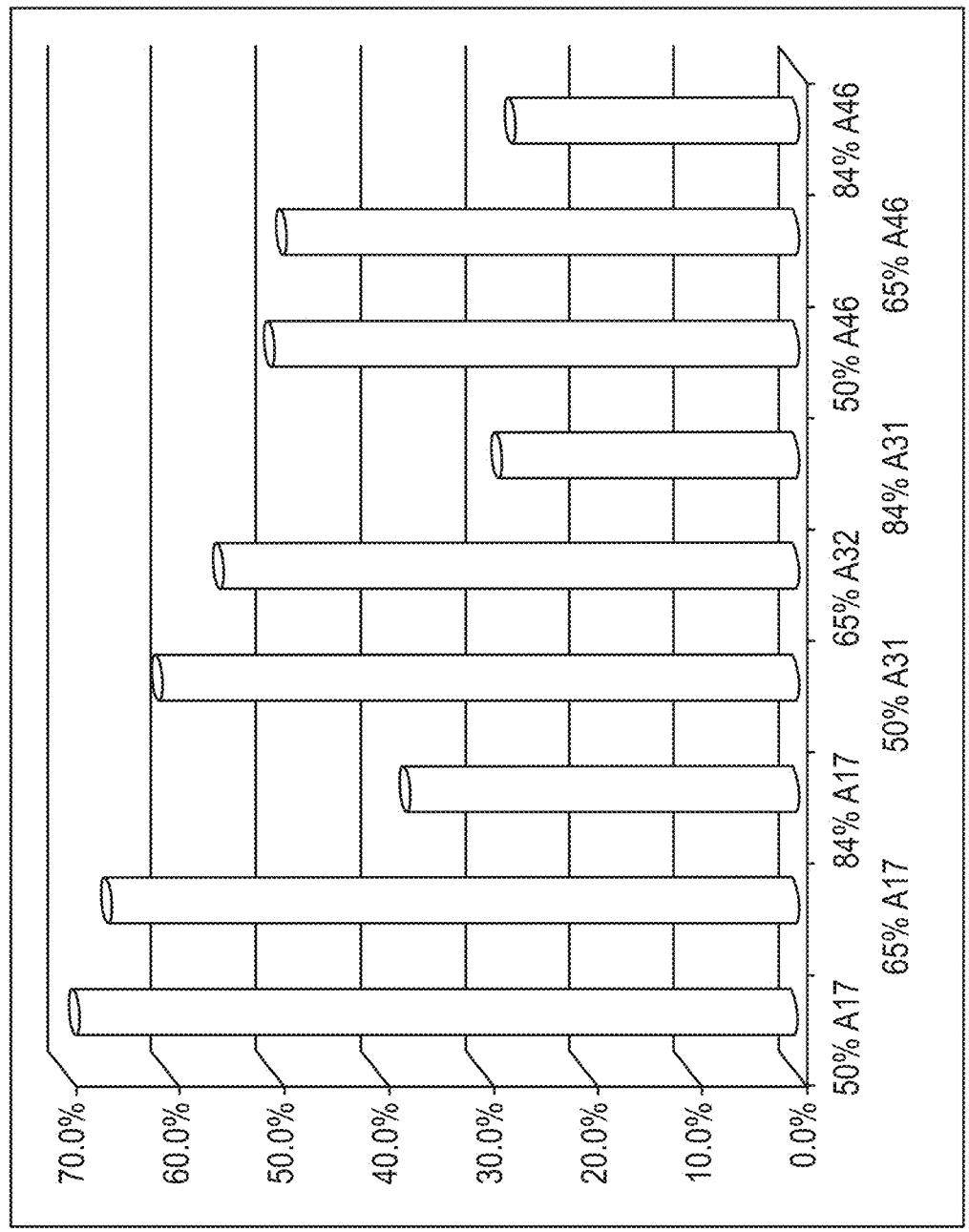
FIG. 1 is a bar graph illustrating various propellant concentrations v. percent fragrance deposition.

There appears to be a non-linear relationship in FIG. 1 between the amount of fragrance deposited at 84% propellant concentration and 65% propellant concentration compared to the amount of fragrance deposited at the 65% propellant concentration and the 50% propellant concentration. This relationship appears generally consistent across the three propellant types. It is believed that, in some instances, an improvement in fragrance deposition may be achieved at propellant concentrations less than about 70%, 68%, 65%, 60%, 55%, or 50% by weight of the total fill of materials. This data might also suggest that it is possible to reduce the concentration of the liquid fragrance material by about 40% to 50% as propellant concentration drops from 84% to within the range of 70% to 65% while still maintaining about the same amount of liquid fragrance deposition on skin.

Confoundingly, decreasing propellant concentration may involve a number of negative tradeoffs. First, the lower antiperspirant composition dilution that accompanies decreasing propellant concentration may result in an antiperspirant composition/liquid propellant mixture that has a higher concentration of particulates than a more diluted mixture. This may increase the risk of clogging within the small passages and orifices of a spray device. Second, increasing the antiperspirant composition mass flow rate too much may lead to over-dosing, which in turn can negatively impact skin feel (e.g., lead to a wet or sticky feel from the presence of too much antiperspirant active on skin) and/or increase the likelihood of a visible residue. Third, it may be desirable to reduce the size of the one or more orifices and/or other flow areas within the container in order to prevent too high of an antiperspirant mass flow. Reducing the size of these flow areas may increase the risk of clogging however. Fourth, decreasing the propellant concentration may diminish the cool/fresh feeling at time of application due to less liquid propellant depositing on the skin and subsequently vaporizing there from.

Propellant pressure is another design variable that may also affect the mass flow of the antiperspirant composition/liquid propellant mixture. Different propellants will have different equilibrium pressures within the head space of a reservoir. For example, A-46 (which is typically a mixture of isobutane, butane and propane) has an equilibrium pressure of 46 psig (317 kPa) while A-31 (which is isobutane) has an equilibrium pressure of 31 psig (213 kPa). As propellant pressure within the head space decreases, the mass flow of the antiperspirant composition/liquid propellant mixture correspondingly decreases (all other variables such as flow path design being constant).

It is believed that propellant concentrations less than 30% by weight of the total fill of the container may result in too high of a mass flow of the antiperspirant composition. While reducing the controlling orifice size/area within the container may help offset some of the antiperspirant composition mass flow increase from reducing propellant concentration, propellant concentrations less than 30% may require orifice sizes that are so small that they may become susceptible to clogging and/or which may be more challenging to manufacture in a cost effective manner for commercial products. It is also believed that higher propellant concentrations (e.g., greater than about 65-70% by weight of the total fill of the container) may result in undesirable solubilization of liquid fragrance materials in the propellant and/or otherwise lead to a continued reduction in the deposition efficiency of the antiperspirant composition due to lower antiperspirant composition mass flow and/or the propensity for dispersion of more antiperspirant composition in the form of a gassy cloud.

The propellant may have a concentration from about 30%, 32%, 34% 36%, 38%, 40%, or 42% to about 70%, 65%, 60%, 58%, 56%, 54%, 52%, 50%, 48%, 46%, 44%, or 42% by weight of the total fill of materials (i.e., propellant and antiperspirant composition) stored within the spray device. The amount of liquid propellant (in grams) stored within a container may be from about 4 g, 6 g, 8 g, 10 g to about 50 g, 25 g, 20 g, or 15 g. The volume of liquid propellant stored within the container may be from about 10 ml, 20 ml, 30 ml, or 40 ml to about 100 ml, 80 ml, 70 ml, 60 ml, or 50 ml.

A wide variety of propellants may be used with the spray devices and antiperspirant compositions described herein, although in some embodiments the spray device is substantially free of compressed gas propellants such as nitrogen, air and carbon dioxide. Some suitable propellants may have a boiling point (at atmospheric pressure) within the range of from about −45° C. to about 5° C. Some suitable propellants may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), HFO1234 (trans 1,3,3,3-tetrafluoropropene) and 152A (1,1 difluoroethane).

In some embodiments, it may also be desirable to provide a mixture of propellants having different boiling points. Combining a primary propellant(s) having a boiling point less than 5° C. with a secondary propellant(s) having a boiling point above 5° C. may increase the likelihood of more liquid propellant reaching the skin surface. This in turn may enhance the cool/fresh sensation at time of application due to the vaporization of the additional liquid propellant (e.g., the secondary propellant) from the skin. The secondary propellant may have a concentration from about 1% to about 20%, or from about 1% to about 15%, or from about 2% to about 10% by weight of the total fill of materials in the product. The secondary propellant(s) may have a boiling point from about 5° C., 10° C., 15° C., 20° C., or 25° C. to about 40° C., 35° C., or 30° C. In some embodiments, the secondary propellant(s) may have a boiling point greater than room temperature, or from 25° C. to 40° C., which can further increase the likelihood that the secondary propellant(s) reaches the skin and vaporizes thereat. Two non-limiting propellants suitable for use as secondary propellants include pentane and isopentane, although other propellants having boiling points within the ranges described herein may also be used.

II. Antiperspirant Compositions

A. Antiperspirant Composition Viscosity

In some embodiments, it may be desirable for the viscosity of the antiperspirant composition to be from about 1,000 centipoise, 2,000 centipoise, or 3,000 centipoise to about 50,000 centipoise 40,000 centipoise, or 30,000 centipoise, or 20,000 centipoise, or 10,000 centipoise, or 7,000 centipoise, 5,000 centipoise or 4,000 centipoise at 25° C. (1 centipoise being equal to $1 \times 10^{-3}$ Pa·s). It is believed that a viscosity lower than 1,000 centipoise may lead to an antiperspirant composition, which when spayed, results in a runny or drippy effect on skin. This may be perceived by a user as having a wet rather than dry feel. For comparison, roll-on type antiperspirant compositions often have viscosities below 1,000 centipoise, because the roll-on applicator utilizes a roller ball to apply a thin film of the antiperspirant composition thereby minimizing a runny or drippy effect.

Figure 13:
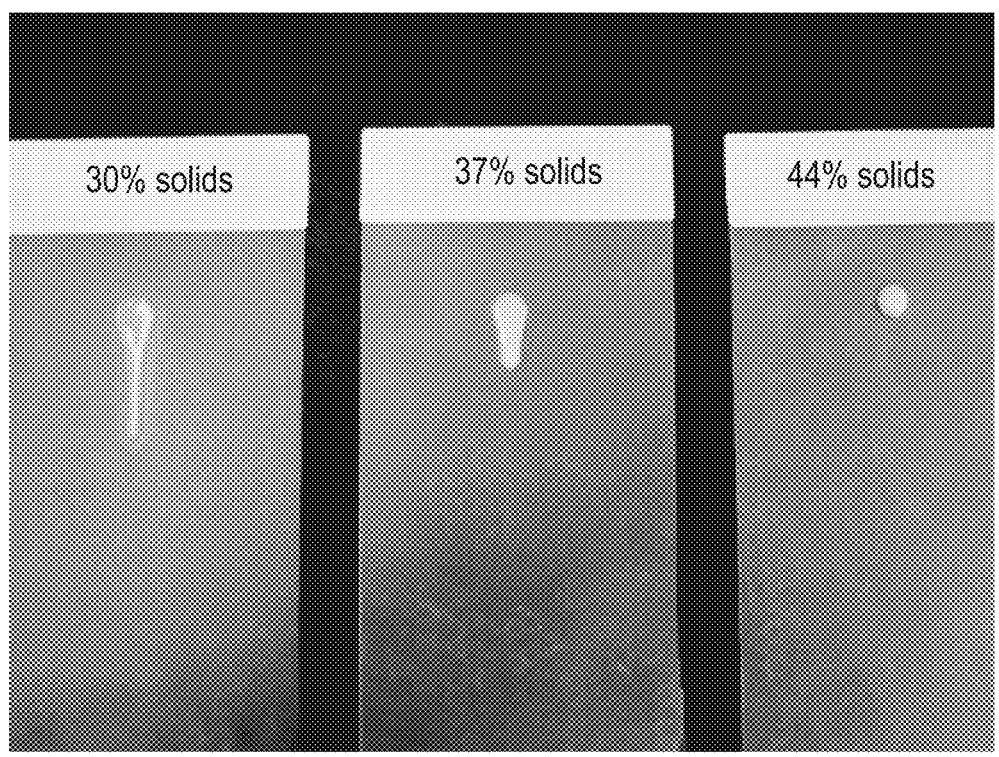
FIG. 13 is a photograph of three antiperspirant compositions, each having a different total particulate concentration, after spraying on a skin mimic material.

By way of illustration, three antiperspirant compositions (Examples 1, 2 and 3) were prepared, each having a different total particulate concentration and, therefore, viscosity. Example 1 comprised 30% total particulates, and Example 2 comprised 37% total particulates while Example 3 comprised 44% total particulates. The composition of Example 1 had a viscosity of about 950 centistokes, the composition of Example 2 had a viscosity of about 2,050 centistokes while the composition of Example 3 had a viscosity of about 5,500 centistokes. Approximately 0.1 ml of each antiperspirant composition was applied to a skin mimic using a syringe. The skin mimic samples were then positioned vertically for approximately 10 seconds. FIG. 13 is a photograph taken of the skin mimic samples after approximately 10 seconds in the vertical position. It can be seen that the composition of Example 1 was very "runny" and had an average drip length more than triple that of the composition of Example 3. The antiperspirant composition of Example 1 approximated that of a roll-on type antiperspirant product and is believed to have poor aesthetics for use in an aerosol antiperspirant product. The antiperspirant composition of Example 3 exhibited good aesthetics and is believed to be acceptable for use in an aerosol antiperspirant product.

Since an antiperspirant composition should be flowable so that it may be sprayed effectively from a spray device, the antiperspirant composition may be devoid of ingredients in sufficient concentrations that an antiperspirant stick or gel type rheology is provided. Some common agents which may be excluded in meaningful amounts include hydrogenated castor oil, solid paraffins, silicone waxes, and mixtures thereof.

B. Non-Volatile Silicone Fluids

The antiperspirant compositions comprise one or more non-volatile silicone fluids. The non-volatile silicone fluid may function as the primary or principal liquid carrier for the antiperspirant active. As used herein, the term "non-volatile" refers to a material that has a boiling point above 250° C. (at atmospheric pressure) and/or a vapor pressure below 0.1 mm Hg at 25° C. Conversely, the term "volatile" refers to a material that has a boiling point less than 250° C. (at atmospheric pressure) and/or a vapor pressure about 0.1 mm Hg at 25° C. Incorporating a non-volatile silicone fluid in an antiperspirant composition may provide several benefits. First, any antiperspirant composition that remains within the container downstream of or within the valve may be subject to drying, particularly when a volatile liquid carrier is used. This tends to be less of an issue at higher propellant concentrations as more propellant is available for expansion and purging of the valve and actuator openings of the antiperspirant composition prior to drying. However, at lower propellant concentrations, build-up and drying of antiperspirant composition may become more prevalent, which can in turn increase the risk of clogging. Incorporating a non-volatile silicone fluid in the antiperspirant composition may reduce the risk of drying within the container post use. Second, incorporating a non-volatile silicone fluid may increase the substantivity of the antiperspirant composition on skin, thereby potentially increasing antiperspirant efficacy, as the antiperspirant composition may form a film that more readily adheres to skin rather than flaking off or transferring to clothing. Third, incorporating a non-volatile silicone fluid may also decrease the propensity for a visible residue to appear on skin (compared to using a volatile silicone fluid), as the non-volatile silicone fluid does not evaporate thereby leaving behind the white antiperspirant active as a visible residue. However, incorporating a non-volatile silicone fluid is not without potential tradeoffs. A perception of wetness post application (which may be undesirable for some consumers) is one tradeoff that may be associated with high concentrations of a non-volatile silicone fluid in an antiperspirant composition.

The total concentration of non-volatile, silicone fluids may be from about 30%, 35%, 40%, 45%, 50% to about 70%, 65%, 60%, 55% or 50% by weight of an antiperspirant composition. In some embodiments, the total concentration of non-volatile, silicone fluids may be from about 35% or 45% to about 55% by weight of an antiperspirant composition. The liquid materials of the antiperspirant composition may consist essentially of or primarily comprise a non-volatile, silicone fluid(s). Some non-volatile, silicone fluids that may be used include, but are not limited to, polyalkyl siloxanes, polyalkylaryl siloxanes, and polyether siloxane copolymers, and mixtures thereof. Some preferred non-volatile silicone fluids may be linear polyalkyl siloxanes, especially polydimethyl siloxanes (e.g., dimethicone). These siloxanes are available, for example, from Momentive Performance Materials, Inc. (Ohio, USA) under the tradename Element 14 PDMS (viscosity oil). Silicones Fluids from Dow Corning Corporation (Midland, Mich., USA) available under the trade name Dow Corning 200 Fluid series (e.g., 3 to 350 centistokes). Other non-volatile silicone fluids that can be used include polymethylphenylsiloxanes. These siloxanes are available, for example, from the General Electric Company as SF 1075 methyl phenyl fluid or from Dow Corning as 556 Fluid. A polyether siloxane copolymer that may be used is, for example, a dimethyl polyoxyalkylene ether copolymer fluid. Such copolymers are available, for example, from the General Electric Company as SF-1066 organosilicone surfactant. The non-volatile, silicone fluid may have an average viscosity from about 3 centistokes, 5 centistokes, 10 centistokes, 20 centistokes, or 50 centistokes to about 350 centistokes, 200 centistokes, 100 centistokes, 50 or 30 centistokes at 25° C. (1 centistoke being equal to $1 \times 10^{-6}$ m$^2$/s). In some specific embodiments, the silicone fluid may have a viscosity from about 5 centistokes to about 100 centistokes or 5 centistokes to about 50 centistokes or about 5 centistokes to about 30 centistokes. Higher viscosity non-volatile silicone fluids (e.g., greater than 100 centistokes or 200 centistokes or 350 centistokes) are preferably mixed with lower viscosity, non-volatile silicone fluids to achieve an appropriate antiperspirant composition viscosity in combination with the concentration of particulates. High viscosity, non-volatile silicone fluids (e.g., greater than 100, 200, or 350 centistokes) may comprise less than 25% by weight of an antiperspirant composition.

In some instances, the non-volatile silicone fluid is a polydimethylsiloxane fluid (also commonly referred to as dimethicone). It will be appreciated that a polydimethylsiloxane fluid may be further characterized by, optionally, its viscosity or its molecular weight or its formula or a combination thereof. In some instances, the polydimethylsiloxane fluid may have the following characteristics:

TABLE 1

| Viscosity | Approximate Molecular Weight[1] | Approximate Average Number of Monomer Units in the Polymer[1] |
|---|---|---|
| 3 Centistokes | 500 | 6 |
| 5 Centistokes | 800 | 9 |
| 10 Centistokes | 1200 | 13 |
| 20 Centistokes | 2000 | 27 |
| 30 Centistokes | 2600 | 35 |
| 50 Centistokes | 3800 | 50 |
| 100 Centistokes | 6000 | 80 |
| 200 Centistokes | 9400 | 125 |
| 350 Centistokes | 13,700 | 185 |

[1]The compositions of Examples 1 to 24 and FIGS. 1 to 12, to the extent they contained a dimethicone fluid, were formulated utilitizing a Dow Corning DC200 series fluid, which is believed to have had average molecule weights and average number of monomer subunits falling within the approcximate values of above-described table.

The polydimethylsiloxane fluid may have the following formula (II):

M-D$_X$-M wherein M is (CH$_3$)$_3$SiO and D is 2CH$_3$(SiO) and X is equal to the average number of monomer units (see, e.g., Table 1) in the polymer minus 2. In some embodiments, X may be from about 6 to about 185, from about 9 to about 125, from about 9 to about 80, from about 9 to about 50, from about 13 to about 50 or from about 27 to about 50. In other embodiments, X may be from about 6 to about 35, from about 9 to about 35 or from about 13 to about 35. The term "approximate" as used in Table 1 refers to ±10% of a given value.

While a wide variety of non-volatile silicone fluids or oils may be used in an antiperspirant composition, in some instances it may be desirable for the non-volatile silicone fluid(s) to consist essentially of or consist of or consist primarily of non-functionalized silicone fluids. In some embodiments, it may be further desirable for the non-volatile silicone fluid(s) to be substantially or completely free of non-functionalized siloxanes capable of reacting with the antiperspirant active via an acid-base reaction or a chelation reaction. This is in contrast to, for instance, U.S. Pat. No. 4,806,338 which proposes the use of functionalized siloxanes. Functionalized siloxanes may in some instances be disadvantageous in that they may react with the antiperspirant active, either via an acid-base reaction in the case of aminofunctional silicones, which are Lewis bases (the antiperspirant actives are Lewis acids), or via a chelation reaction (in the case of the carboxy functional silicones), which reactions can reduce the efficacy of the antiperspirant active. In addition, functional silicones of the type taught by U.S. Pat. No. 4,806,338 may have reduced solubility in the propellant (and vice versa) which may give rise to inhomogeneity in the product with resultant inhomogeneity of deposition on skin.

C. Liquid Fragrance Materials

An antiperspirant composition may also optionally comprise one or more liquid fragrance materials. Liquid fragrance materials are typically a mixture of perfume or aromatic components that are optionally mixed with a suitable solvent, diluent or carrier. Some suitable solvents, diluents or carriers for the perfume components may include ethanol, isopropanol, diethylene glycol monoethyl ether, dipropylene glycol, diethyl phthalate, triethyl citrate, isopropyl myristate and mixtures thereof. An antiperspirant composition may comprise from about 0.5%, 0.75%, 1%, 2%, 3% or 4% to about 10%, 8%, 6%, or 4%, 3% or 2% by weight of a liquid fragrance material.

The perfume component may be any natural or synthetic perfume component known to one skilled in the art of creating fragrances including, but not limited to, essential oils, citrus oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Some non-limiting examples of perfume components include: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenyl-carbinyl acetate, p-tert.butyl-cyclohexyl acetate, isononyl acetate, vetiveryl acetate, vetiverol, alpha-n-amylcinammic aidehyde, alpha-hexylcinammic aldehyde, 2-methyl-3-(p-tert.butylphenyl)-propanol, 2-methyl-3-(p-isopropylphenyl)-propanal, 3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyltetrahydropyran, methyldihydrojasmonate, 2-n-heptylcyclopentanone, 3-methyl-2-pentylcyclopentanone, n-decanal, 9-decenol-1, phenoxyethyl isobutyrate, phenyl-acetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylionones, irones, cis-3-hexenol and esters thereof, indane musk fragrances, tetralin musk fragrances, isochroman musk fragrances, macrocyclic ketones, macrolactone musk frangrances, ethylene brassylate, aromatic nitro-musk fragrances. Some perfume components are also described in Arctander, Perfume and Flavour Chemicals (Chemicals), Vol. I and II (1969) and Arctander, Perfume and Flavour Materials of Natural Origin (1960).

D. Other Liquid Materials

While it may be desirable for the liquid materials of the antiperspirant composition to consist essentially of or be primarily formed from non-volatile silicone fluids, it is contemplated that other liquid materials may be optionally included in an antiperspirant composition. The liquid materials of the antiperspirant composition may comprise less than 30%, 20%, 10%, or less than 5% by weight of liquid materials other than non-volatile, silicone fluids. Said in another way, the liquid materials of the antiperspirant composition may comprise more than 70%, 75%, 80%, 85%, 90% or about 100% by weight of non-volatile silicone fluids.

It is believed that an antiperspirant composition whose liquid materials comprise too much of a volatile silicone fluid may lead to an increased propensity for the appearance of a residue due to the evaporation of the volatile silicone fluid. An antiperspirant composition may comprise less than 10%, 5%, 1%, or 0.5% by weight of a volatile silicone fluid. An antiperspirant composition may be substantially or completely free of a volatile silicone fluid.

An antiperspirant composition may optionally comprise one or more silicone gums. The term "gum" is used to refer to a material that has a viscosity within the range from about 100,000 to about 100 million centistokes at 25° C. and which slowly flowable, as opposed to a rigid solid, which is not flowable, or a liquid, which is too flowable. Some examples of silicone gums include, but are not limited to, quaternary ammonium functional silicones such as DC7-6030 available from Dow Corning and 34720, 34749, 34731, 33134, SF-96, SF-1066, SF18 (350), SE30 and SE32 available from General Electric. A silicone gum may be added to an antiperspirant composition to further increase substantivity of the antiperspirant composition and/or increase the drop size of the aerosol spray particles. However, formulating an antiperspirant composition with a silicone gum in combination with relatively high concentrations of a non-volatile silicone fluid and/or relatively high concentrations of total particulates may involve a number of tradeoffs. For example, too much of a silicone gum may dramatically increase viscosity of the antiperspirant composition and the risk of clogging of the container actuator and/or valve, particularly where there is already a relatively high concentration of total particulates. Still further, too much of a silicone gum may reduce the diameter of the spray making it more difficult for a user to achieve complete coverage of an axillia (typically a 7.5 cm×12.5 cm area) during application as well as potentially creating regions of high antiperspirant composition dosage, thereby potentially impacting skin feel. Further, some silicone gums, such as the quaternary ammonium functional silicones described in U.S. Pat. No. 7,815,899 may have an undesirable odor (e.g., a fish-like odor) associated therewith, which may then be imparted to an antiperspirant composition in some instances.

Examples 4 to 9 illustrate the effect that silicone gum concentration may have on spray pattern. The antiperspirant compositions of Examples 4 to 9 comprised different concentrations of a silicone gum mixture (12% dimethiconol in dimethicone), ranging from 0.5% (Example 4) to 12% (Example 9) by weight of the antiperspirant composition. The antiperspirant compositions were sprayed on a black paperboard and the spray pattern diameter and characteristics were noted. It is believed that the spray pattern produced by Example 9 is poor for use in an aerosol antiperspirant product, while the spray patterns of Examples 5, 6 and 7 are acceptable. The spray patterns of Examples 4 and 8 were marginally acceptable. Different propellants (e.g., with a lower vapor pressure, such as A-17) might improve the spray pattern of Example 4 while Example 8 might improve with A-46. Generally, it is believed that as propellant concentration and/or propellant vapor pressure increase, a higher concentration of gum may be useful.

Given the one or more potential challenges associated with incorporating a gum and more particularly a silicone gum, an antiperspirant composition may be substantially or completely free of gum materials. When inclusion of one or more gums is desirable, an antiperspirant composition may have a total concentration from about 0.05% or 0.075% to about 1%, 0.75%, 0.5%, 0.4%, 0.3%, or 0.2% of gums by weight of the antiperspirant composition. The gum may have a viscosity from about 100,000 centistokes to about 10,000,000 centistokes at 25° C.

If a silicone gum is included, any silicone gum having a viscosity within the ranges described herein may be used, provided it is soluble in the liquid carrier, propellant or a combination thereof of the antiperspirant composition. Some suitable silicone gums include silicone polymers of the dimethyl polysiloxane type, which may have other groups attached, such as phenyl, vinyl, cyano, or acrylic, but the methyl groups should be in a major proportion. Silicone polymers having a viscosity below about 100,000 centistokes (molecular weight below about 100,000) at 25° C. are not considered silicone gums here but are rather, typically, considered a silicone fluid. One non-limiting example of silicone gum suitable for use is a silicone/gum fluid blend comprising a dimethiconol gum having a molecular weight form about 200,000 to 4,000,000 along with a silicone fluid carrier with a viscosity from about 0.65 to 100 mm$^2$ s$^{-1}$. An example of this silicone/gum blend is available from Dow Corning, Corp. of Michigan, USA under the trade name DC-1503 Fluid (88% dimethicone fluid/12% dimethiconol). Other silicone gums materials include SF1236 Dimethicone, SF1276 Dimethicone, and CF1251 Dimethicone available from Momentive Performance Materials, Inc. of NY, USA.

An antiperspirant composition is preferably substantially or completely free of water added as separate ingredient (i.e., anhydrous), as too much added water may result in several deleterious effects such as: 1) increasing the propensity for antiperspirant active particulates to agglomerate (thereby increasing the propensity for clogging), and 2) reducing dry feel on skin. It will be appreciated that even an anhydrous antiperspirant composition may still contain some water that is bound with an ingredient (e.g., antiperspirant active, tapioca material, etc.) otherwise added to the antiperspirant composition.

E. Particulate Materials

While the combination of low propellant concentration and a high concentration of non-volatile silicone fluids may provide a number of benefits, this combination may also involve a number of tradeoffs. For example, higher antiperspirant active deposition (facilitated by a low propellant concentration) in combination with a high concentration of a non-volatile silicone fluid may result in a wet and/or sticky skin feel. In addition, a non-volatile silicone fluid may tend to impede release of the antiperspirant active more so than a volatile liquid carrier, as a volatile liquid carrier eventually evaporates leaving behind the antiperspirant active and the other non-volatile components, which are easily wetted by perspiration thereby releasing the antiperspirant active. In contrast, non-volatile silicones do not evaporate as easily and tend to be hydrophobic, thereby potentially decreasing antiperspirant active release.

Delivering a sufficient concentration of particulates to the skin is believed to improve the skin feel of an antiperspirant composition comprising a high concentration of a non-volatile silicone fluid. It is believed that an antiperspirant composition comprising a total non-volatile liquid material to total particulate material ratio (L/P ratio) from about 0.6, 0.8, 1, 1.2, or 1.4 to about 1.6, 1.4, 1.2 or 1 may balance the tradeoff between enough particulates to provide acceptable skin feel while minimizing the appearance of residue. An antiperspirant composition may have a total particulate concentration from about 30%, 35%, or 40% to about 50% or 45% by weight of the antiperspirant composition.

The antiperspirant composition may comprise a variety of particulate materials. However, it is believed that the type (e.g., hydrophilic v. hydrophobic) and concentrations of particulate materials included in an antiperspirant composition may, in some instances, impact skin feel, release of the antiperspirant active, and the propensity for clogging in the spray device. For example, too much antiperspirant active may result in a wet or sticky skin feel due to the propensity of antiperspirant actives to become sticky when hydrated (e.g., by perspiration) even within the L/P ratios previously described. In addition, too much of a hydrophobic particulate material may reduce release of the antiperspirant active from the composition. Conversely, inclusion of a hydrophilic particulate material may advantageously aid release of the antiperspirant active, which may be beneficial in a composition comprising a high concentration of a non-volatile silicone fluid. However, hydrophilic materials may increase the risk of clogging in the presence of water. Therefore, it may be desirable to balance these and other design considerations when incorporating particulate materials in an antiperspirant composition comprising a non-volatile silicone fluid that is in turn used in a spray device with low propellant concentration.

Referring to Examples 10 to 15, various antiperspirant compositions comprising a non-volatile silicone fluid and having different total particulates, total liquids and liquid to particulate ratios were analyzed for the amount of visible residue provided by the the antiperspirant composition. L/P ratios of 0.5, 0.8, 1, 1.4, 1.9 and 3.6 were tested. L/P ratios less than 1 are believed to provide very good feel characteristics (see, e.g., Example 3, wherein 44% solids and an L/P ratio of 1.27 provided minimal runniness). From Examples 10 to 15, it is believed that increasing L/P ratios tends to reduce the appearance of visible residue in an antiperspirant composition comprising a non-volatile silicone fluid and, further, that L/P ratios greater than about 1 may be particularly beneficial, as there appears to be a significant decrease in the appearance of residue at an L/P ratio of about 1 (e.g., comparing Examples 12 and 13) and thereafter. Therefore, it is believed that L/P ratios from about 1 to about 1.6 may be particularly beneficial in some instances for balancing the tradeoff between skin feel and residue in an antiperspirant composition comprising a non-volatile silicone fluid.

Some examples of particulate materials suitable for use include, but are not limited to, antiperspirant actives, powders (e.g., starch materials), encapsulated fragrance materials and bulking or suspending agents (e.g., silicas or clay materials). Other types of particulates may also be incorporated in an antiperspirant composition.

Antiperspirant Actives

An antiperspirant composition comprises one or more antiperspirant actives. The antiperspirant actives are in a particulate form (rather than being solubilized) in the antiperspirant composition. Therefore, it may be desirable that the antiperspirant composition is provided in a form other than an emulsion or is substantially or completely free of solubilizers for the antiperspirant active. The antiperspirant composition may be provided in the form of a liquid dispersion (including suspensions and colloids). This is in contrast to, for instance, WO 03/002082 which discloses solubilizing the antiperspirant active in an emulsion having a disperse phase and a continuous phase. Since the amount of antiperspirant active may significantly impact skin feel, an antiperspirant composition may comprise from about 16%, 18%, 20%, 22%, or 24% to about 34%, 32%, 30%, 28%, or 26% by weight of a particulate antiperspirant active. In some instances, it may be desirable to utilize a low concentration of the antiperspirant active, such as less than 20% or 18% by weight of the antiperspirant composition. The antiperspirant active concentrations refer to the anhydrous amount that is added.

Referring to Examples 16 to 23, various antiperspirant compositions were prepared with differing concentrations of antiperspirant active particulates, non-volatile silicone fluid, total particulate concentrations and antiperspirant active particulate concentration to total particulate concentration. It is believed that high concentrations of antiperspirant active particulates and/or high antiperspirant active concentration to total particulate concentration ratios (A/P) may result in antiperspirant compositions that are undesirably sticky and/or which may result in undesirable clumping or balling of the antiperspirant active particulates when wetted by a sweat event. A small amount of water was added to the antiperspirant compositions to simulate a sweat event and the amount of tack associated with antiperspirant composition post wetting was measured. Comparing Examples 16 and 17 (both of which had the same concentration of dimethicone but differing total solids), the tack associated with the antiperspirant composition of Example 17 increased significantly to a level believed to be too sticky. The antiperspirant composition of Example 17 had an A/P ratio of 0.9 and an antiperspirant active particulate concentration of 40%. Comparing Examples 18, 19 and 20, the antiperspirant compositions of Examples 18 and 19 had acceptable tack scores while the antiperspirant composition of Example 20 was believed to be too sticky. The antiperspirant composition of Example 20 had an A/P ratio of 0.94 and an antiperspirant active particulate concentration of 48%. Comparing Examples 21, 22 and 23, the antiperspirant composition of Example 21 was believed to be acceptable while the antiperspirant compositions of Examples 22 and 23 had some clumping when wetted. The antiperspirant composition of Example 23 had an A/P ratio of 0.86 and an antiperspirant active particulate concentration of 50%. It is believed that antiperspirant active particulate concentrations greater 35%, 40%, 45% or 50% may result in undesirable stickiness and/or clumping in use when the A/P ratio is greater than 0.8, 0.85, 0.9 or 0.95. Said another way, it may be desirable for the antiperspirant composition to have an A/P ratio less than about 0.95, 0.9, 0.85 or 0.8, or from about 0.1 or 0.3 to about 0.75, 0.7, 0.6 or 0.5.

The antiperspirant active may represent the highest concentration of particulate materials in the antiperspirant composition. For example, the antiperspirant active (on an anhydrous basis) may comprise from about 50% to about 80%, or from about 50% to about 70%, or from about 50% to about 60% of the total particulate materials in the antiperspirant composition. The balance of the total particulate concentration comprises non-antiperspirant active particulates. Some examples of suitable antiperspirant actives include astringent metallic salts, particularly including the inorganic and organic salts of aluminum. Some non-limiting examples exemplary aluminum salts that can be used include aluminum chloride and the aluminum hydroxyhalides having the general formula $Al_2(OH)_aQ_b\cdot XH_2O$ where Q is chloride, bromide, or iodide (preferably chloride), a is from about 2 to about 5, and a+b=about 6, and a and b do not need to be integers, and where X is from about I to about 6, and X does not need to be an integer. Particularly preferred are the aluminum chlorhydroxides referred to as "5/6 basic chlorhydroxide" wherein "a" is 5 and "2/3 basic chlorhydroxide" wherein "a" is 4. Aluminum salts of this type can be prepared in the manner described more fully in U.S. Pat. Nos. 3,887,692; 3,904,741; and 4,359,456. Preferred compounds include the 5/6 basic aluminum salts of the empirical formula $Al_2(OH)_5Dl_2H_2O$; mixtures of $AlC_{136}H_2O$ and $Al_2(OH)_5Cl_2H_2O$ with aluminum chloride to aluminum hydroxychloride weight ratios of up to about 0.5. Some examples of antiperspirant actives include, but are not limited to aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, aluminum zirconium trichlorohydrate, aluminum zirconium tretrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium octachlorohydrex glycine and combinations thereof. In some instances, the aluminum salt may be prepared by methods well known in the art. In some embodiments, the aluminum salts may be made by applying heat to a dilute aqueous solution of an aluminum salt (e.g., less than 20% of an aluminum salt by weight of the dilute solution) to form a solid aluminum salt comprising aluminum hydrolysis polymers. Some non-limiting examples of such methods are described in U.S. Pat. Nos. 4,871,525 and 4,359,456.

Substantially Inert Particulate Materials

The balance of the total particulate concentration of an antiperspirant composition may comprise excipient particulate materials that are substantially inert with respect to itself and/or antiperspirant active, meaning there are no significant particle to particle interactions with respect to itself and/or the antiperspirant active when present in the antiperspirant composition. Excipient particulate materials exclude clays and silicas added to an antiperspirant composition as bulking or suspending agents, as these particles can exhibit strong particle to particle interactions. The excipient particulate materials may be either hydrophilic or hydrophobic (including hydrophobically modified, which tend to be moderately hydrophobic). Some non-limiting examples of substantially inert excipient particulate materials that may be included in an antiperspirant composition include, but are not limited to, encapsulated fragrance materials; native starches such as tapioca, corn, oat, potato, and wheat starch particulates; talc; calcium carbonate; perlite; mica and polyethylene beads. The substantially inert particulates may be free flowing. An antiperspirant composition may comprise from about 0.25%, 0.5%, 1%, 5%, 10%, 12%, or 14% to about 25%, 22%, 20%, 18%, or 16% by weight of the antiperspirant composition of substantially inert particulates. One substantially inert particulate material believed to be suitable for use is a hydrophilic or hydrophobically modified tapioca starch material. A tapioca starch material may be particularly beneficial as it is unlikely to induce an allergic reaction if inhaled. Tapioca is a starch which may be extracted from the cassava plant, typically from the root, which may then be processed or modified as known in the art. Tapioca starches are, advantageously, substantially non-allergenic. One non-limiting example of a hydrophobically modified tapioca starch material suitable for use comprises a silicone grafted tapioca starch, which is available under the trade name Dry Flo TS from AkzoNobel of the Netherlands. The INCI name is tapioca starch polymethylsilsesquioxane and may be produced by a reaction of methyl sodium siliconate (polymethylsilsesquioxane) and tapioca starch. This silicone grafted tapioca starch material is commercially available as CAS No. 68989-12-8. The silicone grafted tapioca starch material can be formed using any known means, including, but not limited to those methods described in U.S. Pat. Nos. 7,375,214, 7,799,909, 6,037,466, 2,852,404, 5,672,699, and 5,776,476. Other non-limiting examples of hydrophobically modified tapioca starch materials that are suitable for use include Dry Flo AF (silicone modified starch from Akzo Nobel), Rheoplus PC 541 (Siam Modified Starch), Acistar RT starch (available from Cargill) and Lorenz 325, Lorenz 326, and Lorenz 810 (available from Lorenz of Brazil). In some specific embodiments, the tapioca starch material may be hydrophilic in order to facilitate release of the antiperspirant active during use. One non-limiting example of a hydrophilic tapioca starch material suitable for use is available under the trade name Tapioca Pure available from Akzo Nobel. In some specific embodiments, the substantially inert particulate material comprises a hydrophilic tapioca material, a hydrophobic tapioca material or a mixture thereof.

An antiperspirant composition may optionally comprise one or more particulate fragrance carriers or materials that may or may not encapsulate a perfume component. Fragrance carriers are typically particulates, which would be considered part of the total particulate concentration of the antiperspirant composition. The fragrance carriers are preferably hydrophobic in order to minimize particle-to-particle interactions. The fragrance carriers may be either full or empty. A full fragrance carrier is a fragrance carrier that encapsulates or otherwise contains a perfume component while the fragrance carrier is stored within the spray device. Full fragrance carriers may release their perfume components by a variety of mechanisms post delivery from the spray device to provide a desired aroma or fragrance experience for a user. For example, the perfume components may be released by moisture upon wetting of the fragrance carrier, e.g., by perspiration or other body fluids. Alternatively or in addition thereto, the perfume components may be released by fracture of the carrier, such as by the application of pressure or a shearing force. An empty fragrance carrier is a fragrance carrier that does not contain a perfume component while stored within the spray device. One non-limiting example of an empty fragrance carrier is an uncomplexed cyclodextrin material.

Some non-limiting examples of fragrance carriers suitable for encapsulating a perfume component include, but are not limited to, oligosaccharides (e.g., cyclodextrins), starches, polyethylenes, polyamides, polystyrenes, polyisoprenes, polycarbonates, polyesters, polyacrylates, vinyl polymers, silicas, and aluminosilicates. Some examples of fragrance carriers are described in USPNs 2010/0104611; 2010/0104613; 2010/0104612; 2011/0269658; 2011/0269657; 2011/0268802; U.S. Pat. Nos. 5,861,144; 5,711,941; 8,147,808; and 5,861,144.

An antiperspirant composition may comprise from about 0.25%, 0.5%, 0.75%, 1%, or 2% to about 20%, 16%, 12%, 10%, 8%, 6% or 4% by weight of the antiperspirant composition of fragrance carriers. In some instances, the substantially inert excipient particles of the antiperspirant composition consist essentially of or completely of full fragrance carriers, empty fragrance carriers, or mixtures thereof. An antiperspirant composition may comprise from about 0.25%, 0.5%, 0.75%, or 1% to about 6%, 4% or 2% by weight of the antiperspirant composition of full fragrance carriers. An antiperspirant composition may comprise from about 0.25%, 0.5%, 1%, or 2% to about 16%, 12%, 10%, 8%, 6% or 4% by weight of the antiperspirant composition of empty fragrance carriers. In some instances, it may be desirable to incorporate a mixture of empty fragrance carriers and full fragrance carriers in the antiperspirant composition, wherein the empty fragrance carriers may be included to achieve the desired overall particulate concentration without the risk of perfume over-dosing.

In some instances, it may be desirable to provide a mixture of fragrance carriers and native starch powders to achieve the desired particle concentration. For example, from about a 20:80 to 80:20 (fragrance carrier to starch) mixture might be utilized. In some instances, a 50:50 mixture might be utilized and in other instances the native starch powders might have a concentration equal to about or less than 6% by weight of the antiperspirant composition while the concentration of the fragrance carriers might be equal to about or less than 9% by weight of the antiperspirant composition.

A wide variety of perfume components may be used with the fragrance carriers, including but not limited to volatile perfume components having a boiling point at normal pressure of less than about 260° C., more preferably less than about 250° C., and perfume components having significant low odor detection threshold, and mixtures thereof. The boiling points of many perfume components are given in, e.g., "Perfume and Flavor Chemicals (Aroma Chemicals)," Steffen Arctander, published by the author, 1969.

Bulking and Suspending Agents

An antiperspirant composition may comprise a bulking or suspending agent. In some instances, it may be desirable to include a bulking or suspending agent in the antiperspirant composition in order to reduce the risk of caking of the antiperspirant composition at the bottom of the container and/or to aid in the redispersion of the antiperspirant composition upon shaking without significant clumping so as to reduce the risk of clogging any small orifices within the spray device. This may be particularly useful as antiperspirant actives are dense and tend to settle quickly and/or may be prone to caking in the presence of moisture. Significant settling and/or agglomeration of particulates in an antiperspirant composition may complicate delivery of a uniform dose of the antiperspirant active from a spray device. This in turn may negatively impact skin feel or contribute to the appearance of a white residue. While other solutions for addressing redispersion, settling and/or caking may be employed, there may also be tradeoffs involved. For example, U.S. Pat. No. 7,815,899 suggests utilizing a high viscosity polymeric material (e.g., a quaternary ammonium functional silicone) to reduce the settling rate. However, this approach may, in some instances, have tradeoffs. For example, some quaternary silicones have a strong odor from amine impurities that can interfere with fragrance of the product. Moreover, these amines may negatively interact with the active via a lewis acid/base reaction.

The bulking or suspending agent may be hydrophobic, hydrophilic or comprise mixtures thereof. In some specific embodiments, these materials may be hydrophilic in order to facilitate release of the antiperspirant active during use. Some examples of silica materials that may be used include, but are not limited to, colloidal silicas. Some non-limiting examples of silica materials are available from Evonik Industries under the trade names Aerosil 200SP, Aerosil 300SP and Aerosil R972.

In some instances, the antiperspirant composition may include a clay material. Some non-limiting examples of clay materials include montmorillonite clays and hydrophobically treated montmorillonite clays. Montmorillonite clays are those which contain the mineral montmorillonite and may be characterized by a having a suspending lattice. Some examples of these clays include but are not limited to bentonites, hectorites, and colloidal magnesium aluminum silicates. Some non-limiting examples of organoclays include modified bentonite, modified hectorite, modified montorlinite and combinations thereof, some examples of which are available under the trade names Bentone 27 (stearalkonium bentonite), Bentone 34 (stearalkonium bentonite) and Bentone 38 (disteardimonium hectorite) from Elementis Specialities Plc. and Tixogel VPV (quaternium 90-bentonite), Tixogel VZV (stearalkonium bentonite), Tixogel LGM (stearalkonium bentonite) and Claytone SO (stearalkonium bentonite) from Southern Clay Products.

The antiperspirant composition may also comprise a clay activator, such as propylene carbonate, triethyl citrate, methanol, ethanol, acetone, water and mixtures and derivatives thereof. Clay activators may also strongly interact with an antiperspirant active (e.g., leading to clumping or coating of the antiperspirant active and/or changes in active polymer structure which may reduce antiperspirant efficacy). Therefore, it may be desirable to limit the amount of clay activator present in the antiperspirant composition to between about 0.5%, 0.75%, 1%, 1.25%, or 1.5% to about 3%, 2%, or 1.75% by weight of the antiperspirant composition.

III. Spray Devices

In order to avoid over-dosing of the antiperspirant composition, it is desirable that the spray device have a total mass flow rate of the propellant/antiperspirant composition mixture of less than 0.5 grams/sec or from about 0.1 grams/sec to about 0.6 grams/sec, or from about 0.2 grams/sec to about 0.4 grams/sec, or from about 0.25 grams/sec to about 0.35 grams/sec. The spray device may have an antiperspirant composition mass flow rate less than 0.3 grams/sec or from about 0.1 grams/sec to about 0.3 grams/sec or from about 0.1 grams/sec to 0.2 grams/sec or from about 0.15 grams/sec to about 0.2 grams/sec. It is believed that mass flow rates greater than described above may lead to a wet or sticky skin feel (even if the L/P ratio is within the ranges previously described), because the total amount of antiperspirant composition deposited on the skin may be too great.

The amount of antiperspirant active delivered to a target surface by a two second application from a spray device may be from about 40 mg, 50 mg, 60 mg, or 70 mg to about 100 mg, 90 mg, or 80 mg. The total amount of antiperspirant composition delivered to a target surface by a two second application of a spray device may be from about 0.1 grams to about 0.4 grams, or from about 0.2 grams to about 0.4 grams, or from about 0.2 grams to about 0.3 grams. The amount of liquid fragrance material delivered to a target surface by a two second application of a spray device may be from about 3 mg to about 20 mg, or from about 6 mg to about 15 mg, or from about 6 mg to about 12 mg. The amount of full fragrance carriers delivered to a target surface by a two second application of a spray device may be from about 0.75 mg to about 15 mg, or from about 1 mg to about 12 mg, or from about 1 mg to about 9 mg. The spray device may have a deposition efficiency, of either the antiperspirant composition and/or the antiperspirant active and/or the liquid fragrance material, that is from about 60%, 65%, 70%, 75% or 80% to about 95%, 90%, 85% or 80%.

Figure 2:
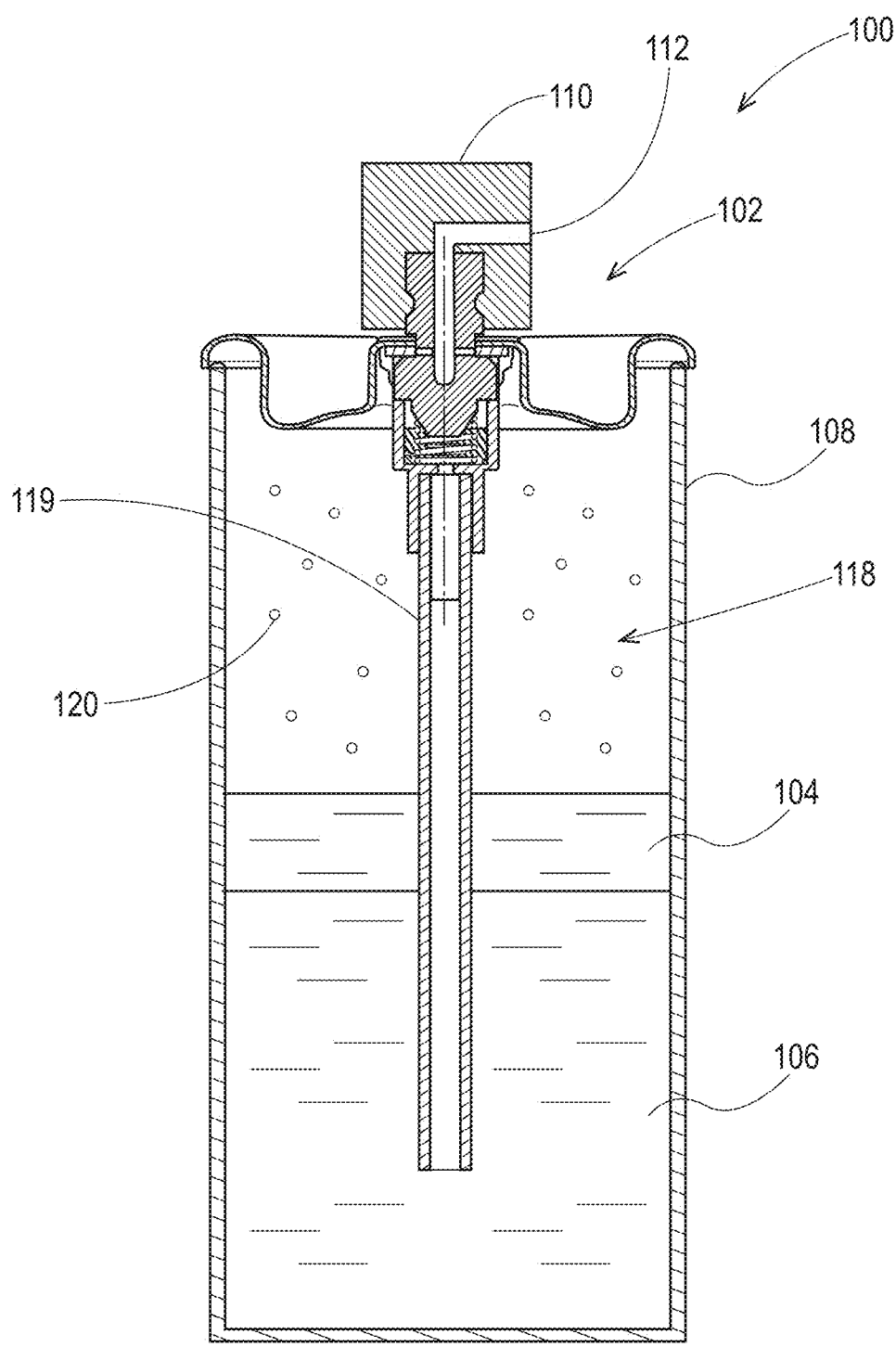
FIG. 2 is a cross-sectional side view of one non-limiting example of a novel spray device comprising an actuator, a valve assembly and a reservoir containing a liquid propellant, a gaseous propellant and an antiperspirant composition.

Referring to FIG. 2, one non-limiting example of a spray device that may be used with the antiperspirant compositions and propellants described herein is shown. While the spray device of FIG. 2 is described hereafter as one spray device suitable for use, it will be appreciated that other spray devices, including other types of actuators and valve assemblies, etc., may also be used with the antiperspirant compositions and propellants described herein. The spray device 100 comprises a container 102, a liquid propellant 104 and an antiperspirant composition 106. It will be appreciated that the propellant 104 and antiperspirant composition 106 are merely shown for purposes of illustration in FIG. 2, and FIG. 2 is not intended to limit in any way the type or arrangement of the propellant and antiperspirant composition within the container 102. For example, in some instances the propellant and the composition are miscible such that distinct layers may not be visible. The spray device 100 may be shaped and configured so that it is hand-holdable. The container 102 comprises a body 108, an actuator 110 having an actuator orifice 112, and a valve assembly 114 in fluid communication with a reservoir 118 storing the composition 106 and liquid propellant 104. The reservoir 118 may be defined by one or more interior surfaces of the body 108. The reservoir may have a volume from about 20 ml, 40 ml, or 60 ml to about 120 ml, 110 ml, 100 ml, or 90 ml. A dip tube 119 may extend into the reservoir 118 from the valve assembly. A gaseous propellant 120 may fill the headspace of the reservoir 118.

Figure 3:
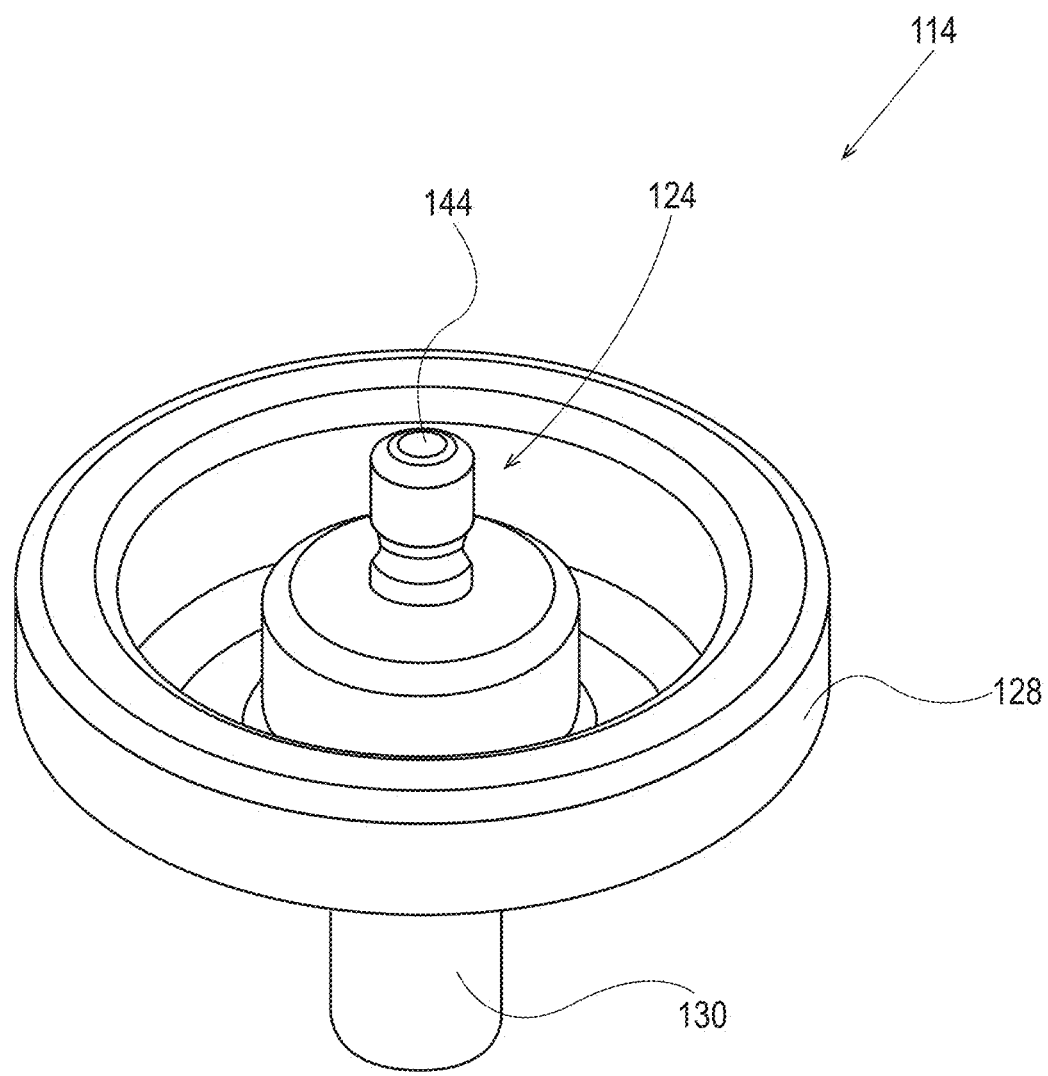
FIG. 3 is a perspective view of the valve assembly of FIG. 2.
Figure 4:
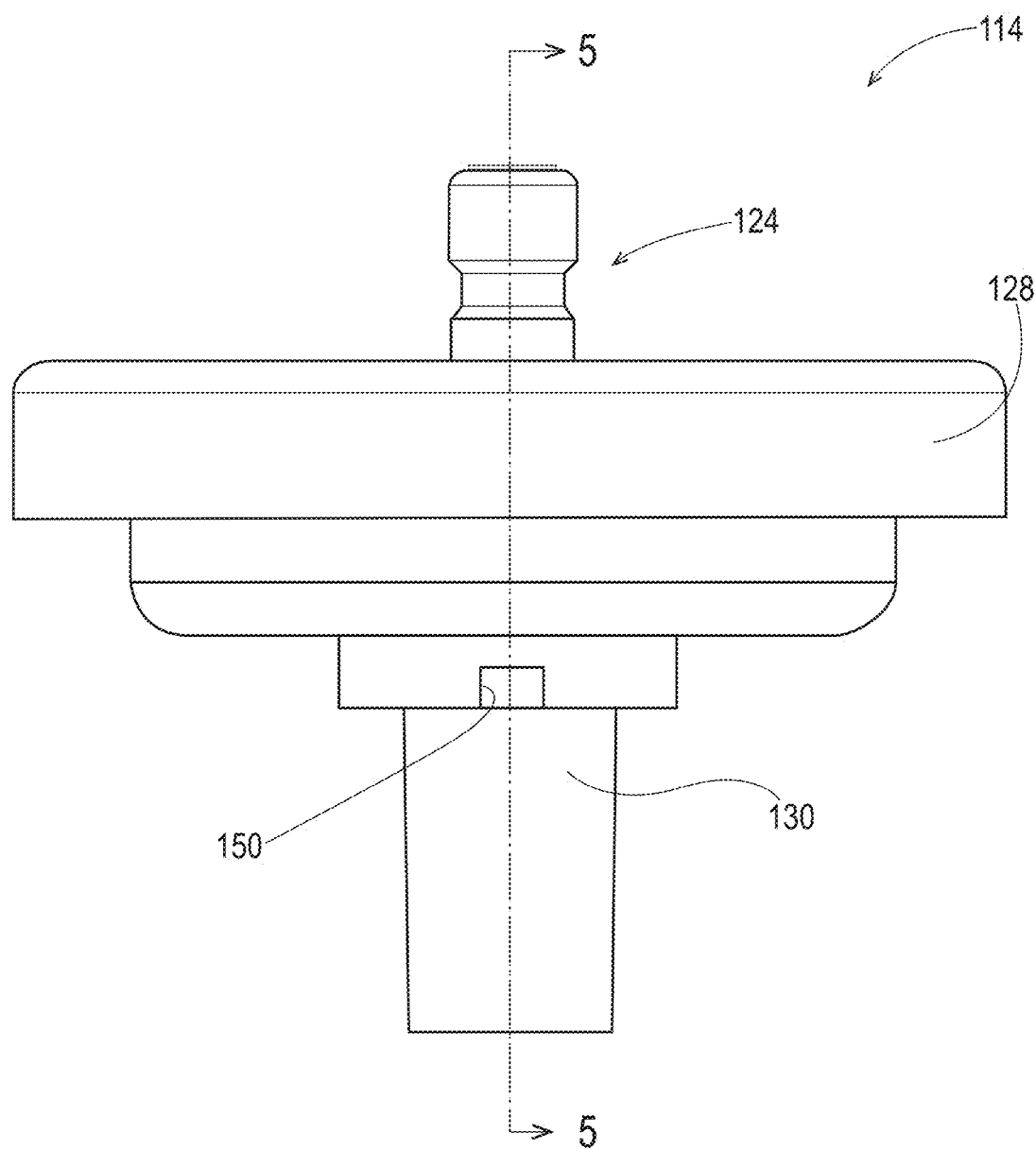
FIG. 4 is a side elevation view of the valve assembly of FIG. 3.
Figure 5:
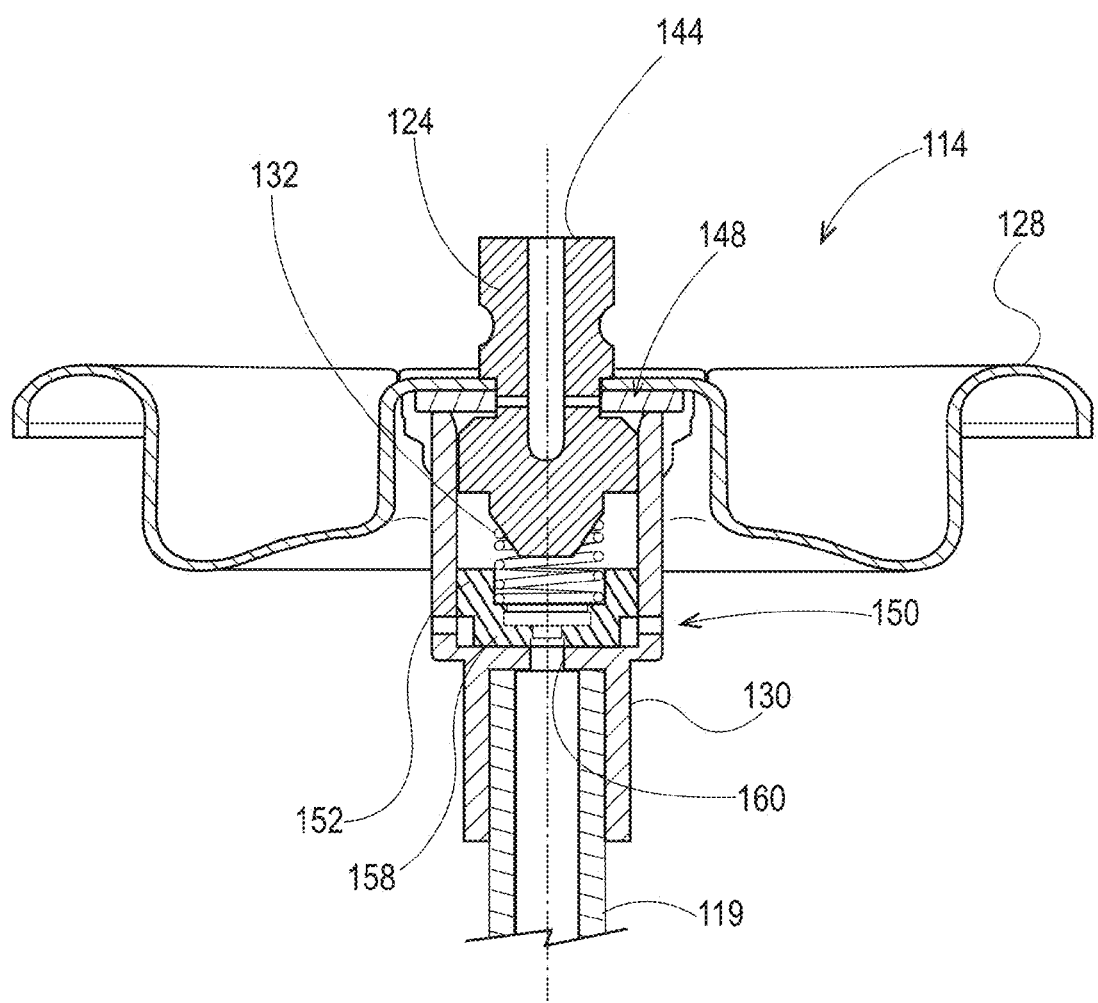
FIG. 5 is a cross-sectional view of the valve assembly of FIG. 4, taken along 5-5 thereof.

Referring to FIGS. 3 to 5, one non-limiting example of a valve assembly 114 which may be attached to the body 108 is shown. The valve assembly 114 comprises a slidably disposed valve stem 124 to which the actuator 110 attaches, a mounting flange 128 for attaching the valve assembly 114 to the body 108 (such as by crimping), and a housing 130 attached to the mounting flange 128. The housing 130 may be attached by a variety of means to the mounting flange, as known in the art, including by a press fit, positive latching, welding, etc. The housing 130 contains a spring 132 that biases the valve stem 124. The spring 132 may comprise a plurality of coils.

Figure 6:
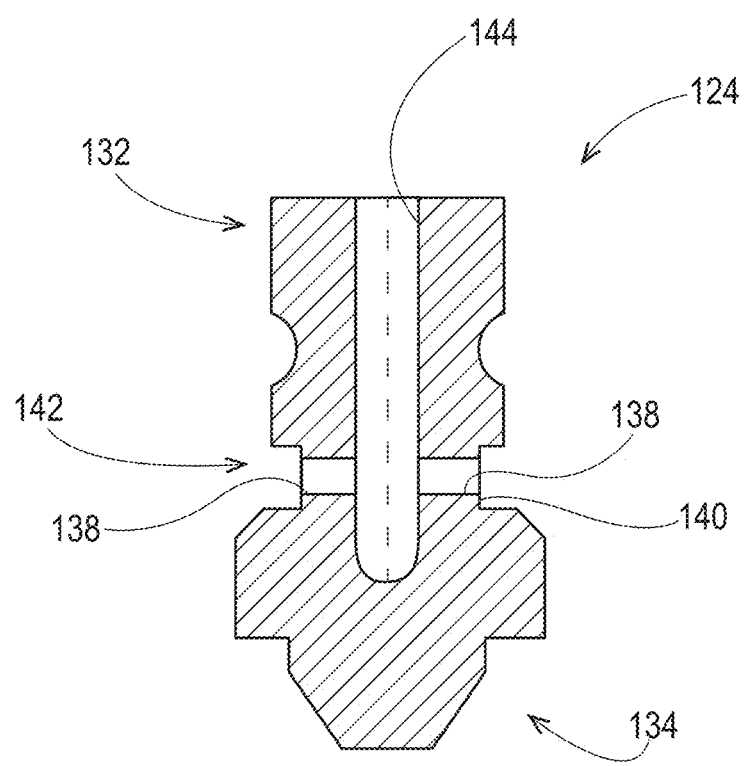
FIG. 6 is cross-sectional side elevation view of the valve stem of FIG. 5.

Turning to FIG. 6, the valve stem 124 comprises an upper portion 132 and a lower portion 134. The upper portion 132 has a distal end and is configured to be attachable to the actuator 110. The lower portion 134 is configured to position at least a portion of the spring 132 there about. One or more valve stem orifices 138 (two being shown in the FIGS.) are disposed between the upper portion 132 and the lower portion 134. The valve stem orifices 138 are arranged in a radial direction with respect to the longitudinal axis of the valve stem 124. The two or more valve stem orifices 138 open into a wall 140 of a groove 142 and communicate with an axial bore 144 that extends from the two or more valve stem orifices 138 to the distal end of the upper portion 132. It will be appreciated that the terms "radial" and "axial", and derivatives thereof (e.g., radially and axially), are intended to merely refer to a general direction with respect to a feature or structure, and these terms are intended, unless expressly stated otherwise (e.g., solely axial or solely radial), to be fully inclusive of directions that are not purely radial or axial, such as substantially radial/axial directions and combinations of radial and axial directions where the net overall directional effect is more radial than axial or vice versa. The axial bore 144 in turn communicates with the actuator 110 when it is attached to the valve stem 124.

Figure 7:
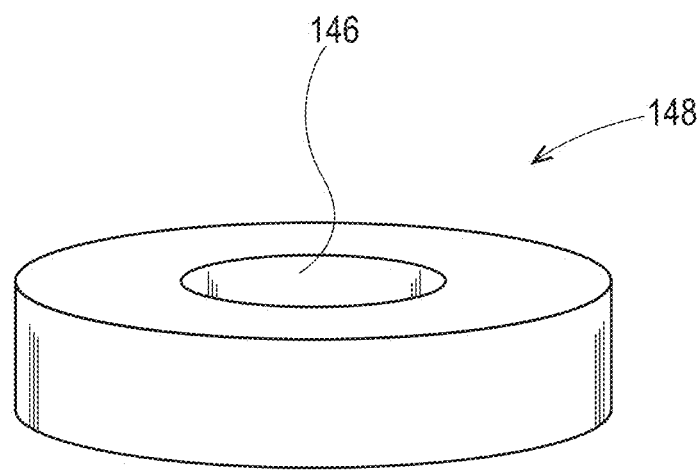
FIG. 7 is a perspective view of the seal of FIG. 5.
Figure 8:
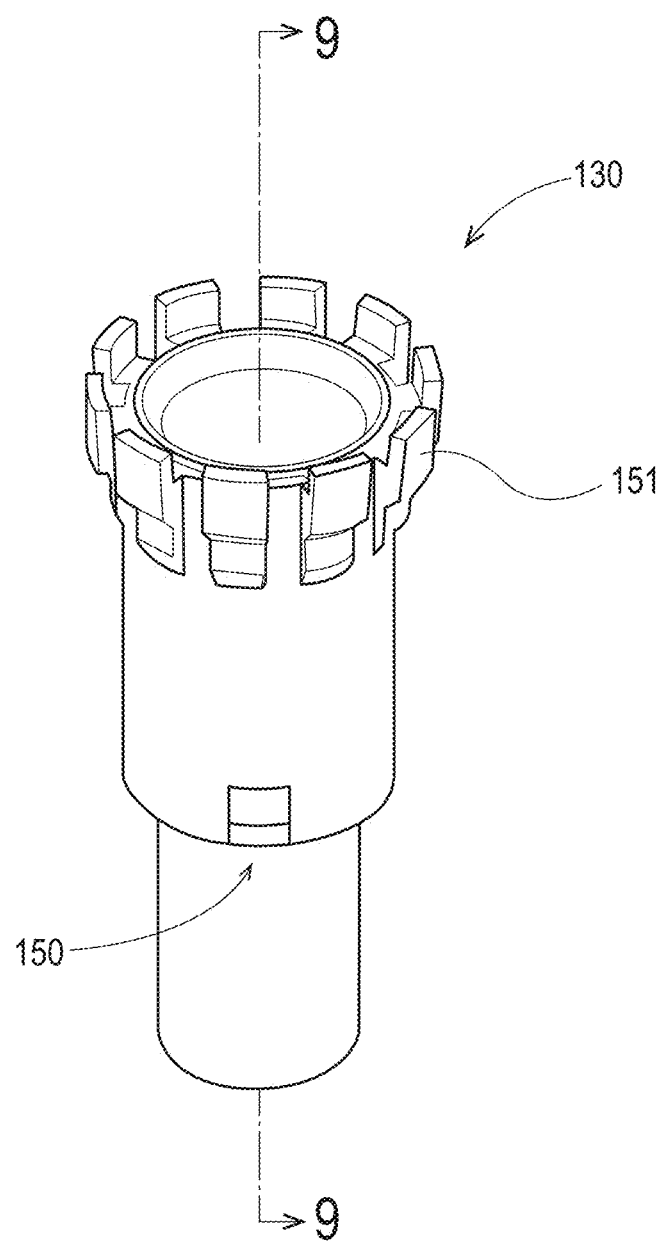
FIG. 8 is a perspective view of the housing of FIG. 5.
Figure 9:
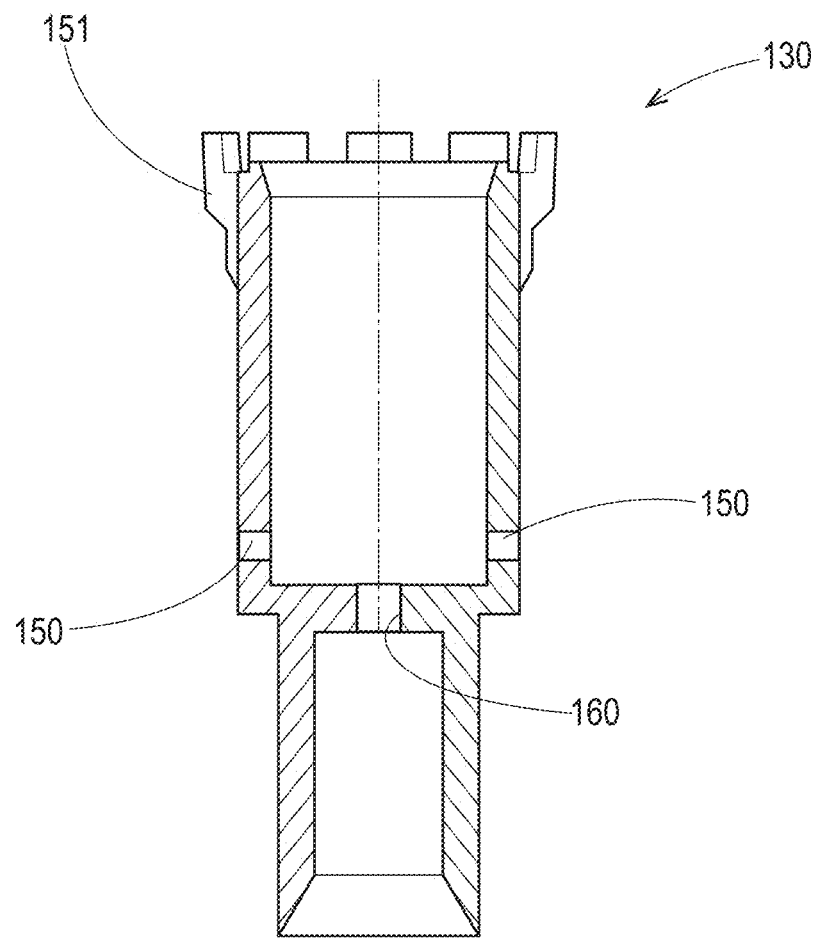
FIG. 9 is a cross-sectional side elevation view of the housing of FIG. 8, taken along line 9-9 thereof.
Figure 10:
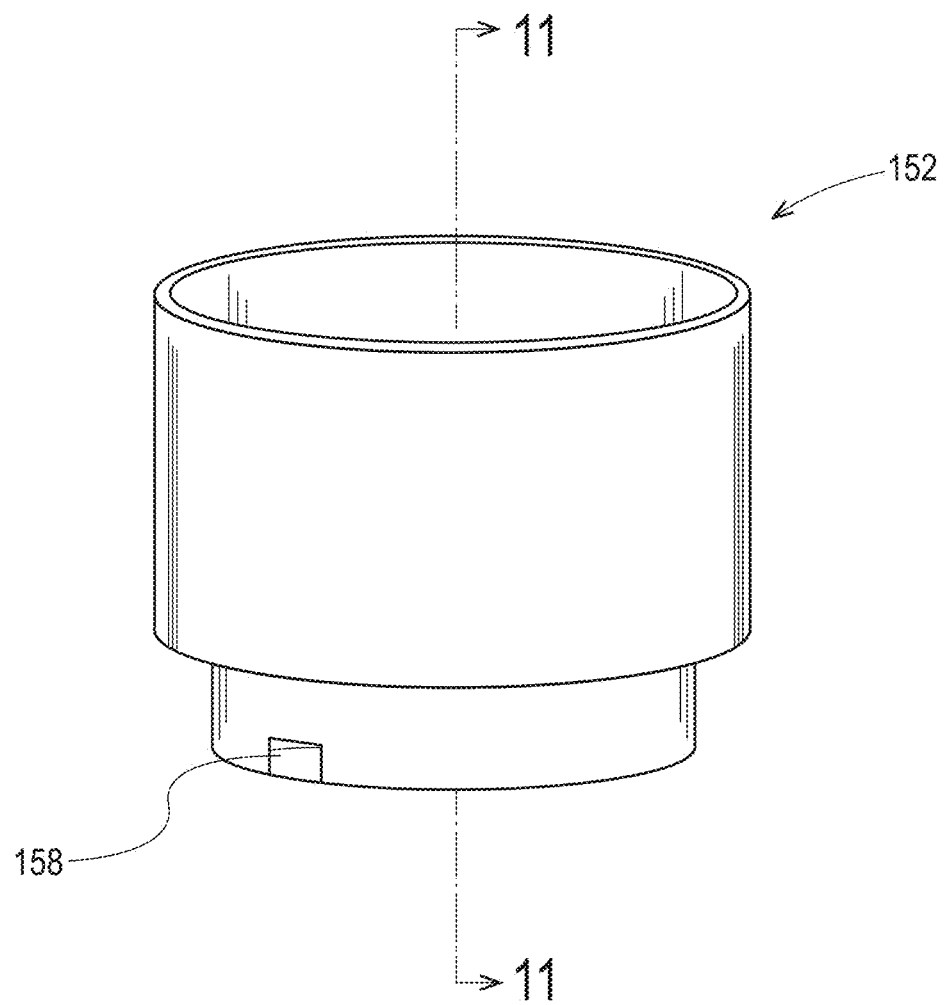
FIG. 10 is a perspective view of the insert of FIG. 5.
Figure 11:
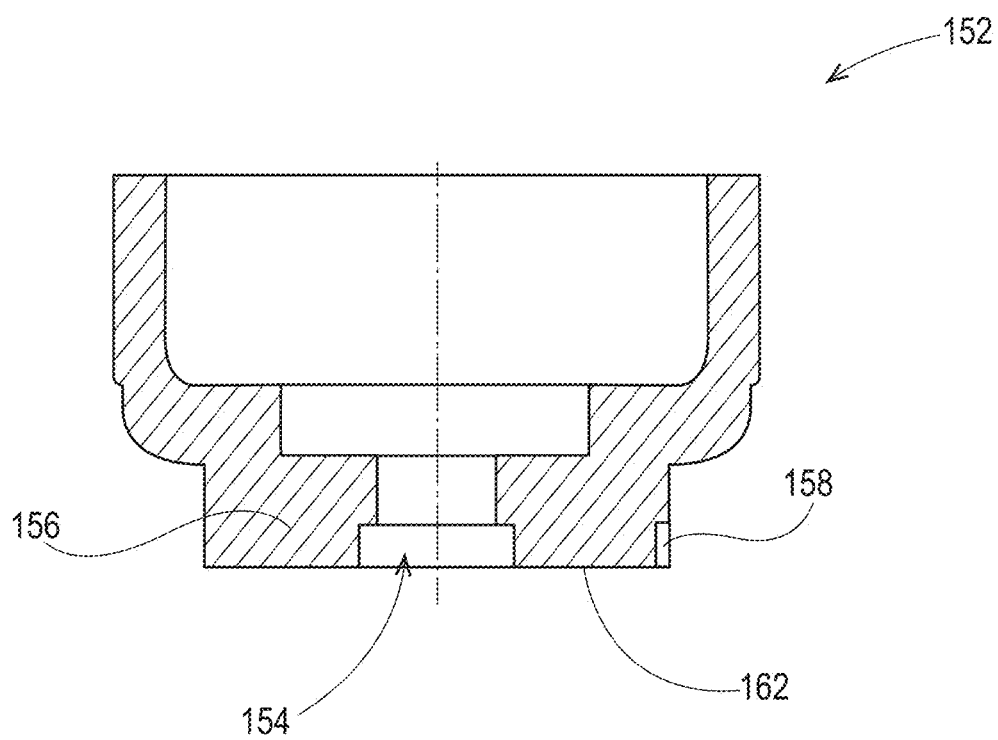
FIG. 11 is a cross-sectional side elevation view of the insert of FIG. 10, taken along line 11-11 thereof.
Figure 12:
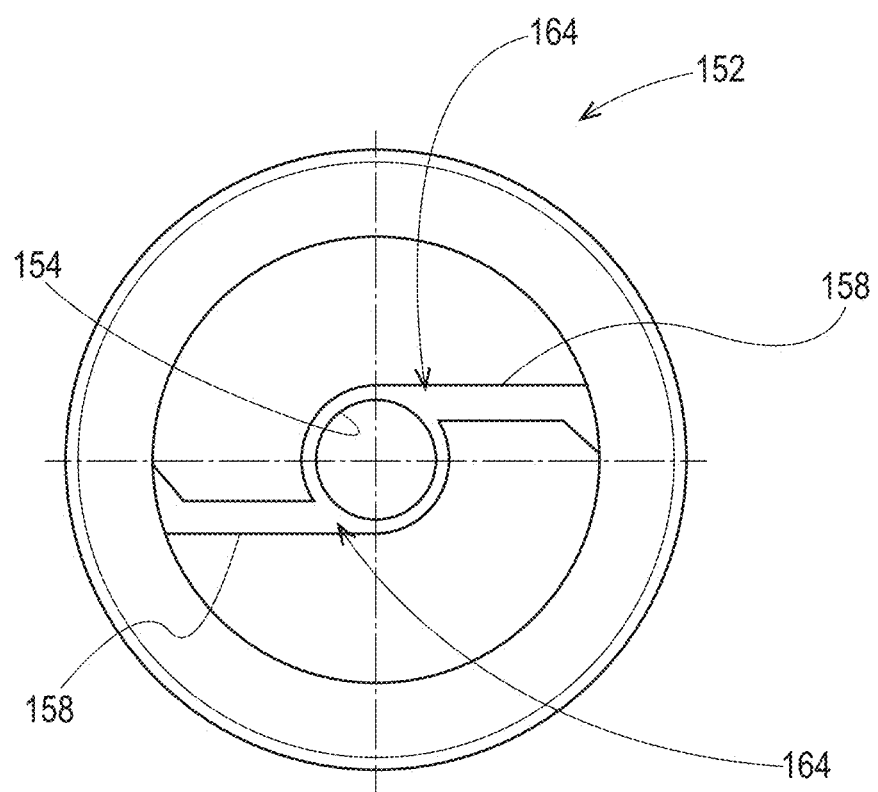
FIG. 12 is a bottom plan view of the insert of FIG. 10.

Referring to FIGS. 2, 5 and 7, mating sealing surfaces formed by an inner wall 146 of a substantially flat seal 148 and the wall 140 of the groove 142 form a valve that seals the valve stem orifices 138. The seal 148 may be formed from an elastomeric material, such as nitrile butadiene rubber (sometimes referred to as Buna-N). The seal 148 may be disposed about the valve stem and sandwiched between the mounting flange 128 and the housing 130, as shown by way of example in FIG. 3. The sealing surfaces are mated when the valve stem is not depressed, as shown in FIG. 3, thereby preventing flow of the antiperspirant composition/liquid propellant mixture thru the valve stem orifices 138. When the actuator 110 is depressed, the sealing surfaces separate, thereby permitting the antiperspirant composition/liquid propellant mixture to flow through the valve stem orifices 138 to the axial bore 144 and onto the actuator 110. As used herein, the term valve (as opposed to valve assembly) is intended to merely refer to the mating sealing surfaces that prevent flow of the antiperspirant composition/liquid propellant mixture from the reservoir 118 to the actuator 110. The mating sealing surfaces may be provided in configurations other than shown in the FIGS and described herein. In some specific embodiments, the valve may be a continuous flow valve, meaning there is flow through the valve for as long as the actuator is depressed. In contrast, a non-continuous or metered valve allows only predetermined amount of flow thru the valve regardless how long the actuator is depressed.

Referring to FIGS. 5 and 8 to 12, the housing 130 comprises one or more holes 150 for permitting gaseous propellant to pass from the head space of the reservoir 118 into the interior of the housing 130. The housing 130 has a plurality of fingers 151 for attaching the housing to the mounting flange 128. An insert 152, which in some embodiments may be cup-shaped, may be installed within the housing 130 between the dip tube and the valve stem 124. The insert 152 may be press-fit within the housing 130 or otherwise retained within the housing by other means known in the art. The insert 152 may receive one end of the spring 132. The insert 152 has an insert bore 154 disposed in a bottom wall 156 of the insert 152. The insert bore 154 is in fluid communication with the dip tube 119 and the interior of the insert 152 so that the antiperspirant composition/liquid propellant mixture may flow from the dip tube 119 to the interior of the insert 152. The mixture then flows past the spring 132 and on to the valve.

A plurality of passages 158 are disposed between the dip tube 119 and the distal end of the valve stem 124. While two passages are shown, it is contemplated that more than two passages may be provided. The passages 158 are disposed adjacent the dip tube exit and/or the tail orifice 160 (FIG. 5), the tail orifice 160 being disposed just downstream of the dip tube exit. For purposes of clarity, the passages 158 of valve assembly 114 are considered to be disposed adjacent the dip tube 119 even though there is an intervening tail orifice 160 located between the dip tube exit and the passages 158. The passages 158 may be disposed in a bottom surface 162 of the bottom wall 156 of the insert 152, and passage exits 164 are disposed adjacent to the insert bore 154 and the tail orifice 160 so that gaseous propellant passing through the passages 158 impinges the antiperspirant composition/liquid propellant mixture exiting the tail orifice 160. While the passages 158 are shown disposed in the bottom surface 162 of the insert, it is contemplated that the passages 158 may be provided by other structures/arrangements. If a vapor tap arrangement is provided, the passage(s) 158 may have a total cross-sectional area from about 0.05 mm$^2$ to about 0.4 mm$^2$.

While the passages 158 are shown as generally rectangular in cross-sectional shape, it will be appreciated that the passages 158 may be provided in other shapes and sizes. Similarly, while the various bores, holes, and orifices are shown and described herein as generally circular/cylindrical in shape, it will be appreciated that they may be provided in other shapes and sizes. Further, while the vapor tap arrangements shown in the FIGS. permit gaseous propellant to mix with the antiperspirant composition/liquid propellant mixture upstream of the valve, other vapor tap arrangements (or no vapor tap) may be implemented as known in the art. For example, a vapor tap arrangement may be provided where the gaseous propellant mixes downstream of the valve, perhaps still within the valve assembly or within the actuator. Multiple vapor tap arrangements may also be provided. For example, a first vapor tap arrangement might provide for mixing of gaseous propellant and the antiperspirant composition/liquid propellant mixture upstream of the valve while a second vapor tap arrangement might provide for mixing of additional gaseous propellant and the antiperspirant composition mixture downstream of the valve. While the valve assembly is shown herein as comprising a variety of components, it is contemplated that these components may be changed, combined, deleted, or other components or structures substituted therefor without departing from the spirit and/or scope of the various invention(s) described herein. For example, the various valve configurations illustrated in U.S. Pat. No. 4,396,152 may also be utilized. Likewise, the container and actuator may be provided in a variety of alternate shapes and configurations.

One example of a valve assembly having the general configuration shown in FIG. 5 is available from the Precision Valve Company (USA) under the trade name Ecosol.

A user of a spray device may initiate a spray by depressing an actuator, thereby opening a valve which enables a liquid propellant/antiperspirant composition mixture to exit the actuator. Prior to actuation, it may be desirable to shake or rotate the product to redisperse the liquid and particulate materials. While usage time can vary widely, users may depress the actuator from about 2 seconds to about 5 seconds, or from about 2 seconds to about 4 seconds, or from about 2 seconds to about 3 seconds to provide a burst of antiperspirant composition for deposition to an underarm or axillia skin surface. A spray device may be sized to provide a total spray time from about 60 seconds to about 200 seconds, or from about 70 seconds to about 150 seconds, for from about 90 seconds to about 130 seconds, thereby providing from about 15 to about 50 two second uses before exhaustion.

IV. Measurement Methods

Propellant Concentration and Antiperspirant Composition Concentration

The overcap (if one is present) of the product container is removed, and the weight of the container and its contents (gross mass) is measured using any suitable scale, such as an analytical balance. The top of the container is punctured using any suitable tool, such as an AC-PD Aerosol Can Puncturing Device available from Aero-Tech Laboratory Equipment Company, LLC of Missouri, USA. The puncture needle is fully extended into the container, and the puncture needle is slowly retracted to permit the gaseous propellant to evacuate the container. Once the puncture needle is completely retracted from the container, the puncturing device can be removed from the container, and the propellant will continue to escape from the puncture in the container. All the propellant is allowed to evacuate from the container.

The mass of the container and the remaining contents (less the propellant) is measured using any suitable device, such as an analytical balance. The actuator is removed from the container using any suitable device, such as an Aero-Tech Can Decrimper available from Aero-Tech Laboratory Equipment Company, LLC of Missouri, USA. The inside of the container is rinsed with ethanol until visually clean and the container is allowed to dry for at least 2 hours. The mass of the empty container and actuator is measured using any suitable device, such as an analytical balance. The propellant mass and concentration may be determined using the following equations:

$$\text{Propellant Mass(g)} = \text{Gross Mass} - \text{Mass After Propellant Evacuation}$$

$$\text{Propellant Concentration \%} = \frac{\text{Propellant Mass}}{\text{Gross Mass} - \text{Mass of Empty Container}}$$

Antiperspirant composition concentration may be derived from the following equation:

$$\text{Antiperspirant Composition Concentration \%} = 100 - \text{Propellant Concentration \%}$$

Total Mass Flow Rate

This measurement method is preferably utilized with aerosol antiperspirant products comprising a continuous actuator, meaning actuating the actuator results in a continuous rather than intermittent spray. At least four aerosol antiperspirant product samples are tested. The product samples are shaken as directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. The product samples are then removed from the bath and excess moisture is removed by blotting with a paper towel. The products samples are shaken if directed and the actuator is actuated for 5 seconds, which may be accurately timed by use of a stopwatch. Each product sample is again weighed, after which the product samples are returned to the constant-temperature bath. The process of bathing, actuating, and weighing is repeated three times for each product sample. The average total mass flow rate may be calculated from the spray time period (5 seconds) and the difference in mass before and after each five second spray, averaged across the four product samples and three repetitions per product sample.

Antiperspirant Composition Mass Flow Rate

This measurement method is preferably utilized with aerosol antiperspirant products comprising a continuous actuator, meaning actuating the actuator results in a continuous rather than intermittent spray. At least four aerosol antiperspirant product samples are tested. The product samples are shaken if directed and then immersed in a constant-temperature (25 C) bath until the internal pressure stabilizes at a temperature of 25° C. The product samples are then removed from the bath and excess moisture is removed by blotting with a paper towel. Each product sample is weighed to measure its mass using any suitable device, such as an analytical balance. Twelve large plastic bags (one for each product sample times three repetitions) having a suitable volume, such as a 1 L Ziploc brand bag (or a Whirl-Pak Write-on 55 ounce bag, Part # B01195WA available from Nasco, Inc), are weighed to measure their mass using any suitable device, such as an analytical balance. Each product sample is shaken if directed and sprayed into one of the bags for a period of 5 seconds in a manner that minimizes antiperspirant composition from exiting the bag. For example, the opening thru which the spray enters the bag may be limited to about 5 cm. The 5 second spray time period may be accurately measured using a stopwatch. Following the 5 second spray period, the antiperspirant composition is allowed to settle within the bag and the bag remains open for at least 1 minute but not longer than 2 minutes in order to allow the liquid propellant to evaporate. The weight of the bags and their contents are weighed to measure their mass, and the product samples are also weighed. The average mass flow rate of the antiperspirant composition may be determined using the following equation which is averaged across the four product samples and the three repetitions per product sample:

Mass Flow Rate of Antiperspirant Composition (g/sec)=(Weight of Bag and Antiperspirant Composition−Weight of Bag)/5 seconds Antiperspirant Composition Deposition Efficiency, Amount Dispensed, and Amount Deposited At least four aerosol antiperspirant product samples are tested. The product samples are shaken if directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. At least twelve filter papers, such as Whatman 150 mm (diameter) Filter Paper available under the catalog number 1003-150 from the Whatman Company of the UK, are weighed to measure the mass of the filter using any suitable device, such as an analytical balance. The product samples are removed from the bath, and any excess moisture is removed by blotting with a paper towel. The product samples are shaken if directed, and the product sample is positioned approximately 15 cm away from one of the filter papers, which is preferably weighted and/or fixtured to assure the filter paper does not move during spraying. The actuator of the product sample is actuated for 5 seconds which may be accurately timed using a stopwatch. It will be appreciated, however, that other spray times may be substituted. For example, a two second spray time period might be used to better approximate the amount dispensed/deposited during a typical use cycle by a consumer. The spray from the product sample should be centered on the center of the filter paper. After spraying, the filter paper and product sample are weighed to measure the mass using any suitable device, such as an analytical balance. The steps of bathing, weighing, and actuating are repeated three times for each of the product samples. The average antiperspirant composition efficiency may be calculated using the following equations, averaged across the four product samples and the three repetitions per product sample:

$$\text{Amount Dispensed(g)} = \text{Product Sample Weight Before Spraying} - \text{Product Sample Weight After Spraying}$$

$$\text{Amount Deposited(g)} = \text{Filter Paper Weight After Spraying} - \text{Filter Paper Weight Before Spraying}$$

$$\text{Antiperspirant Composition Deposition Efficiency}(\%) = 100 \times \frac{\text{Amount Deposited}}{\text{Amount Dispensed} * \text{Antiperpsirant Composition Weight \%}}$$

Antiperspirant Active Deposition Efficiency, Amount Dispensed, and Amount Deposited At least four aerosol antiperspirant product samples are tested. The product samples are shaken if directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. The product samples are then removed from the bath and excess moisture is removed by blotting with a paper towel. At least twelve filter papers, such as Whatman 150 mm Filter Paper available under the catalog number 1003-150 from the Whatman Company of the UK, are weighed to measure the mass of the filter using any suitable devices, such as an analytical balance. The product samples are removed from the bath, and any excess moisture is removed by blotting with a paper towel. The product samples are shaken if directed, and the product sample is positioned approximately 15 cm away from one of the filter papers, which is preferably weighted and/or fixtured to assure the filter paper does not move during spraying. The actuator of the product sample is actuated for 5 seconds which may be accurately timed using a stopwatch. It will be appreciated that other spray times may be substituted. For example, a two second spray time period might be used to better approximate the amount dispensed/deposited during a typical use cycle by a consumer. The spray from the product sample should be centered on the center of the filter paper. After spraying, the filter paper and product sample are weighed to measure the mass using any suitable device, such as an analytical balance. The steps of bathing, weighing, and actuating are repeated three times for each of the product samples. The amount of antiperspirant active deposited on a filter paper may be determined using an automated titrator, such as MettlerDL-70 equipped with Mettler DM141C combination silver-silver chloride electrode available from Mettler, Inc. Alternatively, the amount of antiperspirant active deposited on a filter paper may be determined using the Content of Chloride Method set forth in the USP monograph for aluminum chlorohydrate (USP 35) or an equivalent method. The average antiperspirant active deposition efficiency may be calculated using the following equations, averaged across the four product samples and the three repetitions per product sample:

Amount Dispensed(g) = Product Sample Weight Before Spraying − Product Sample Weight After Spraying Amount Deposited(gm) = Filter Paper Weight Before Spraying − Filter Paper Weight After Spraying $$\text{Antiperspirant Composition Efficiency}(\%) = 100 \times \frac{\text{Amount Deposited}}{\text{Amount Dispensed} * \text{Antiperpsirant Composition Weight \%}}$$

V. Examples

The following examples are given solely for the purpose of illustration and are not to be construed as limitations of the invention as many variations thereof are possible without departing from the spirit and the scope of the invention.

Examples 1, 2 and 3

Examples 1, 2 and 3 illustrate the effect that total particulate concentration may have on viscosity and the effect that viscosity may have on "runniness".

| Ingredient | Example 1 | Example 2 | Example 3 |
|---|---|---|---|
| Aluminum chlorohydrate[1] | 26% | 26% | 26% |
| Dimethicone 50 centistokes | 63.54% | 56.54% | 49.54% |
| Hydrophilic tapioca[2] | 0% | 5% | 12% |
| Disodium Hectorite[3] | 3% | 3% | 3% |
| Triethyl citrate | 0.96% | 0.96% | 0.96% |
| Liquid Perfume | 5.5% | 5.5% | 5.5% |
| Betacyclodextrin fragrance | 1% | 3% | 3% |
| Average Viscosity (centistokes) | 950 | 2050 | 5500 |
| Total Particulate Concentration | 30% | 37% | 44% |
| L/P Ratio | 2.3 | 1.7 | 1.27 |

The values are shown on a by weight of the antiperspirant composition basis.
[1]86% assay of anhydrous active, average particle size approximately 15 microns.
[2]Tapioca Pure available from Akzo Nobel
[3]Bentone 38 available from Elementis The antiperspirarant compositions of Examples 1 to 3 were made using the following general batch method: a first portion of the dimethicone was added to an appropriately sized container followed by the clay and the mixture was milled for at least 2 minutes at a speed of 10,000 to 12,000 rpm using a hand held mill. Triethyl citrate was then added to the mixture and milled for at least 2 minutes. The balance of dimethicone was added to the mixture and milled for at least 2 minutes. The antiperspirant active, tapioca starch, betacyclodextrin fragrance and liquid perfume were added to the mixture and milled for at least 2 minutes.

Approximately 0.1 ml of the antiperspirant compositions of Examples 1, 2 and 3 were deposited, using a syringe, on horizontally positioned skin mimic samples attached to a black paperboard backsheet. A description of the skin mimic material may be found in U.S. Pat. No. 8,124,064 (col. 8, lines 30 to 47). The paperboard backsheet was then rotated to a vertical position for approximately 10 seconds. The drip length was then measured. This process was repeated three times. FIG. 13 is a photograph of one set of three antiperspirant compositions on the skin mimic material after about 10 seconds in the vertical position. The antiperspirant compositions of Example 1 had an average drip length of 40 mm (range=38 mm to 42 mm). The antiperspirant compositions of Example 2 had an average drip length of 20.6 mm (range=20 mm to 22 mm), and the antiperspirant compositions of Example 3 had an average drip length of 11 mm (range=10 mm to 12 mm).

Examples 4 to 9

Examples 4 to 9 illustrate the effect that silicone gum concentration may have on spray pattern.

| Ingredient | Ex 4 | Ex 5 | Ex 6 | Ex 7 | Ex 8 | Ex 9 |
|---|---|---|---|---|---|---|
| Aluminum chlorohydrate[1] | 26% | 26% | 26% | 26% | 26% | 26% |
| Dimethicone - 50 centistoke | 49.04% | 48.54% | 47.54% | 45.545 | 43.54% | 37.54% |
| Hydrophilic tapioca[2] | 12% | 12% | 12% | 12% | 12% | 12% |

-continued

| Ingredient | Ex 4 | Ex 5 | Ex 6 | Ex 7 | Ex 8 | Ex 9 |
|---|---|---|---|---|---|---|
| Disodium Hectorite[3] | 3% | 3% | 3% | 3% | 3% | 3% |
| Triethyl citrate | 0.96% | 0.96% | 0.96% | 0.96% | 0.96% | 0.96% |
| Liquid Perfume | 5.5% | 5.5% | 5.5% | 5.5% | 5.5% | 5.5% |
| Betacyclodextrin fragrance | 3% | 3% | 3% | 3% | 3% | 3% |
| Silicone gum material[4] | 0.5% | 1% | 2% | 4% | 6% | 12% |

The values are shown on a by weight of the antiperspirant composition basis.
[1]86% assay of anhydrous active, average particle size approximately 15 microns.
[2]Tapioca Pure available from Akzo Nobel
[3]Bentone 38 available from Elementis
[4]DC1503 (a mixture of dimethicone and dimethiconol) available from Dow Corning. DC1503 comprises approximately 12% by weight of the mixture of a silicone gum (dimethiconol).

The antiperspirarant compositions of Examples 4 to 9 were made using the following general batch method: a first portion of the dimethicone was added to an appropriately sized container followed by the clay and the mixture was milled for at least 2 minutes at a speed of 10,000 to 12,000 rpm using a hand held mill. Triethyl citrate was then added to the mixture and milled for at least 2 minutes. The balance of dimethicone and the silicone gum material were added to the mixture and milled for at least 2 minutes. The antiperspirant active, tapioca starch, betacyclodextrin fragrance and liquid perfume were added to the mixture and milled for at least 2 minutes. The antiperspirant compositions were added to the product container together with A-31 propellant to achieve a 65% propellant concentration by weight of the total fill of materials. The antiperspirant composition was sprayed onto a black paperboard from a distance of approximately 15.2 cm (6 inches) for approximately 2 seconds. The diameter of the spray pattern and the deposition characteristics are set forth below

| | Spray Diameter (cm) | Observations |
|---|---|---|
| Example 4 | 6 | Gassy spray, even pattern |
| Example 5 | 6 | Even pattern |
| Example 6 | 5.6 | Even pattern |
| Example 7 | 5 | Even pattern |
| Example 8 | 4.5 | Majority of composition within 2 cm of center with a noticeable mound in the center. |
| Example 9 | 3.8 | Majority of composition wihtin 2 cm of center with a large mound of composition in the center |

The antiperspirant compositions were combined with A-46 propellant in a spray device at a ratio of 80% propellant to 20% antiperspirant composition. While this is a higher propellant concentration than other examples, the residue measurements are adjusted for the amount deposited and therefore the observations are believed to be also applicable for lower propellant concentrations. The antiperspirant spray devices were shaken and then the antiperspirant composition was sprayed on a black, artificial leather material (Naugahyde available from Uniroyal Engineered Products LLC) from a distance of about 15 cm (6 inches). The target surface had a size of about 15 cm×10 cm. The spray time was about 4 seconds and the target surface was coated as evenly as possible. The amount of antiperspirant composition deposited on the naugahyde material was determined by weighing the material before and after application of the antiperspirant composition. The L value (L* in the L*A*B* color space) of the antiperspirant composition on the treated naugahyde material was measured at three different locations on the surface using a colorimeter (e.g., Model CR-400 available from Konica-Minolta, Japan). The L values of an untreated naugandye surface were also measured at three locations using the colorimeter. The whiteness of the antiperspirant composition (e.g., observable residue) was approximated by subtracting the average L value derived from three colorimeter measurements of the untreated naugahyde surface from the average L value derived from the three colorimeter measurements of the treated naugahyde surface divided by the amount antiperspirant composition deposited.

Examples 10 to 15

Examples 10 to 15 illustrate the effect that increasing L/P ratio may have on residue for an antiperspirant composition comprising a non-volatile silicone fluid.

Examples 16 to 23

Examples 16 to 23 illustrate the effect that antiperspirant active particulate concentration and/or A/P ratio may have on antiperspirant composition tack following wetting.

| Ingredient | Ex 10 | Ex 11 | Ex 12 | Ex 13 | Ex 14 | Ex 15 |
|---|---|---|---|---|---|---|
| Aluminum chlorohydrate[1] | 30% | 30% | 30% | 25% | 30% | 20% |
| Dimethicone - 50 centistoke | 30.8% | 40.8% | 45.8% | 53.8% | 60.8% | 73.8% |
| Betacyclodextrin fragrance | 3% | 3% | 3% | 0% | 3% | 0% |
| Uncomplexed Betacyclodextrin | 30% | 20% | 15% | 15% | 0% | 0% |
| Disodium Hectorite | 2% | 2% | 2% | 2% | 2% | 2% |
| Triethyl Citrate | 1% | 1% | 1% | 1% | 1% | 1% |
| Perfume | 3.5% | 3.5% | 3.5% | 3.5% | 3.5% | 3.5% |
| Total Particulates | 65% | 55% | 50% | 42% | 35% | 22% |
| L/S ratio | 0.5 | 0.8 | 1 | 1.4 | 1.9 | 3.6 |
| Approximate Residue/g | 327 | 238 | 175 | 42 | 25 | 0.9 |

| Ingredient | Ex 16 | Ex 17 | Ex 18 | Ex 19 | Ex 20 | Ex 21 | Ex 22 | Ex 23 |
|---|---|---|---|---|---|---|---|---|
| Aluminum chlorohydrate[1] | 26% | 40% | 26% | 40% | 48% | 26% | 40% | 50% |
| Dimethicone - 50 centistoke | 48.04% | 48.04% | 32.04% | 32.04% | 32.04% | 35.04% | 35.04% | 35.04% |
| Hydrophilic tapioca[2] | 12% | 0% | 19% | 5% | 0% | 26% | 12% | 2% |
| Disodium Hectorite[3] | 3% | 3% | 3% | 3% | 3% | 3% | 3% | 3% |
| Triethyl citrate | 0.96% | 0.96% | 0.96% | 0.96% | 0.96% | 0.96% | 0.96% | 0.96% |
| Betacyclodextrin fragrance | 3% | 1% | 3% | 3% | 3% | 3% | 3% | 3% |
| Silicone gum[4] | 0.5% | 0.5% | 0.5% | 0.5% | 0.5% | 0.5% | 0.5% | 0.5% |
| A/P ratio | 0.59 | 0.9 | 0.51 | 0.78 | 0.94 | 0.44 | 0.69 | 0.86 |
| Total Particulates | 44% | 44% | 51% | 51% | 51% | 58% | 58% | 58% |
| Average gF | 226 | 342 | 159 | 216 | 253 | 179 | 282 | 182 |

The values are shown on a by weight of the antiperspirant composition basis.
[1] 86% assay of anhydrous active, average particle size approximately 15 microns.
[2] Tapioca Pure available from Akzo Nobel
[3] Bentone 38 available from Elementis
[4] DC1503 (a mixture of dimethicone and dimethiconol) available from Dow Corning. DC1503 comprises approximately 12% by weight of the mixture of a silicone gum (dimethiconol).

Examples 16 to 23 were made using the following general batch method: a first portion of the dimethicone was added to an appropriately sized container followed by the clay and the mixture was milled for at least 2 minutes at a speed of 10,000 to 12,000 rpm using a hand held mill. Triethyl citrate was then added to the mixture and milled for at least 2 minutes. The balance of dimethicone and the silicone gum material were added to the mixture and milled for at least 2 minutes. The antiperspirant active, tapioca starch, betacyclodextrin fragrance and liquid perfume were added to the mixture and milled for at least 2 minutes.

Approximately 0.3 to 0.305 grams of each antiperspirant composition was added to a 6 dram vial after which about 65 microliter of water was added. The vial was sealed and a vortex mixer was used for 1 minute to mix the materials. After mixing, the antiperspirant composition was subjected to the following method to measure its tack or stickiness. The method measures the force (gF) required to separate two surfaces having an antiperspirant composition disposed between them. Lower gram force (gF) measurements being indicative of less stickiness and liquidity (wetness). Measurements are performed using a TA XT plus texture analyzer, such as available from Stable Micro Systems (Surrey England), that utilized a cylinder probe. 25 mm diameter pieces of Leneta card are affixed to both the cylinder probe and base of the actuator. 0.03 to 0.0305 gram of an antiperspirant composition sample was placed between the lineta cards and the instrument is then set to compress the cards together with a 200 gF for 2 seconds and then separated at a speed of 10 mm/sec. The amount of force required to separate the cards is measured as the two are separated. This was repeated 30 times with the first 5 repetitions being averaged to determine a gF for the composition. The average gF values for each antiperspirant composition, along with the concentration of total particulates and the A/P ratio for the antiperspirant composition, are set forth in the table above. The antiperspirant composition of Example 23 contained clumping within the composition as did Example 22 (although less so than observed in Example 23), which is believed to have affected these gF values.

Examples 24, 25, 26 and Comparative Example 27

Examples 24, 25 and 26 further describe and demonstrate some non-limiting examples of antiperspirant compositions made in accordance with the invention, while Example 27 is a comparative antiperspirant composition. The examples are given solely for the purpose of illustration and are not to be construed as limitations of the invention as many variations thereof are possible without departing from the spirit and the scope of the invention.

| Ingredient | Example 24 | Example 25 | Example 26 | Comparative Example 27 |
|---|---|---|---|---|
| Aluminum chlorohydrate[1] | 28% | 28% | 19% | 28% |
| Dimethicone | 48.38% | 52.3% | 61.25% | 5% |
| Cyclopentasiloxane[2] | 0% | 0% | 0% | 47.25% |
| Hydrophobic tapicoa[3] | 12% | 0% | 0% | 0% |
| Hydrophilic tapioca[4] | 0% | 12% | 12% | 12% |
| Disodium Hectorite[5] | 2% | 0% | 0% | 0% |
| Triethyl citrate | 0.67% | 0% | 0% | 0% |
| Silicone gum material[6] | 1% | 0% | 0% | 0% |
| Hydrophilic silica[7] | 0% | 1% | 1% | 1% |
| Hydrophobic silica[8] | 0% | 0.25% | 0.25% | 0.25% |
| Liquid Perfume | 3.5% | 3.5% | 3.5% | 3.5% |
| Betacyclodextrin fragrance | 3% | 3% | 3% | 3% |

The values are shown on a by weight of the antiperspirant composition basis.
[1] 86% assay of anhydrous active, average particle size approximately 15 microns.
[2] DC 200 Fluid (50 cst) available from Dow Corning
[3] Dry Flo TS from Akzo Nobel
[4] Tapioca Pure from Akzo Nobel
[5] Bentone 38 available from Elementis
[6] DC1503 (a mixture of dimethicone and dimethiconol) available from Dow Corning
[7] Aerosil A300 silica from Evonik
[8] Aerosil A300 silica from Evonik The antiperspirarant compositions of Examples 24 to 26 were made using the following general batch method: the non-volatile silicone fluid (and volatile silicone fluid in the case of comparative Example 27) was added to an appropriately sized container followed by the silica (or clay in the case of Example 24) and the mixture was milled for at least 1 minute at a speed of 10,000 to 12,000 rpm using a hand held mill. In the case of Example 24, triethyl citrate was then added to the mixture and milled for at least 5 minutes. The antiperspirant active particles were added to the mixture and milled for at least 1 minute (Examples 25, 26 and 27) or at least 5 minutes (Example 24). The tapioca starch material and betacyclodextrin fragrance were added to the mixture and milled for at least one minute (Examples 25, 26 and 27) or at least 5 minutes (Example 24). The perfume was then added (and in the case of Example 24, the silicone gum) and milled for at least one minute.

Antiperspirant compositions of Example 24 had an average viscosity of approximately 1,500 centipose, and antiperspirant compositions of Example 25 had an average viscosity of approximately 4,200 centipose. Antiperspirant compositions of Example 26 had an average viscosity of approximately 3,000 centipose. Antiperspirant compositions of comparative Example 27 had an average viscosity of approximately 1,400 centipose. The viscosity measurements were made using a Brookfield Viscometer Model 1/2RVT using an RV-4 spindle using techniques well known in the art. The desired weight (approximately 15 g) of the antiperspirant composition was transferred to 55 ml product containers to which a valve assembly was affixed. Approximately 15 g of A-46 propellant was added to the product containers to achieve a 50% propellant concentration and 50% antiperspirant composition concentration by weight of the total fill of materials.

The average pressure within the reservoir was approximately 375 kPa for aerosol products containing the antiperspirant composition of Example 24, and approximately 393 kPA for aerosol products containing the antiperspirant composition of Example 25. The average pressure within the reservoir was approximately 365 kPA for aerosol products containing the antiperspirant composition of Example 26. The average pressure within the reservoir was approximately 379 kPA for aerosol products containing the antiperspirant composition of comparative Example 27. Pressure within the reservoir was measured using a pressure gauge and techniques well known in the art. The valve assembly was similar to that shown in FIGS. 2 to 12, having one radial bore 160 with a diameter of approximately 0.33 mm and two passages 180 each having a width of approximately 0.25 mm and a height of approximately 0.33 mm. An actuator having a discharge orifice 112 with a diametrical dimension of approximately 0.33 mm was fitted on the valve assembly.

Aerosol products comprising the antiperspirant composition of Example 24 had an average total mass flow rate of approximately 0.37 g/sec and an average antiperspirant composition flow rate of approximately 0.17 g/sec. Aerosol products comprising the antiperspirant composition of Example 25 had an average total mass flow rate of approximately 0.38 g/sec and an average antiperspirant composition flow rate of approximately 0.18 g/sec. Aerosol products comprising the antiperspirant composition of Example 26 had an average total mass flow rate of approximately 0.36 g/sec and an average antiperspirant composition flow rate of approximately 0.17 g/sec. Aerosol products comprising the antiperspirant composition of comparative Example 27 had an average total mass flow rate of approximately 0.39 g/sec and an average antiperspirant composition flow rate of approximately 0.18 g/sec.

An in vivo study was conducted using aerosol products comprising the antiperspirant compositions of Examples 24, 25 and 26 and a commercially available aerosol antiperspirant product. The ingredient listing for the commercially available product was as follows: butane, isobutene, propane, cyclomethicone, aluminum chlorohydrate, parfum, disteardimonium hectorite, dimethiconol, PVM/MA copolymer, sodium starch octenylsuccinate, mannitol, alpha-isomethyl ionone, butylphenyl methylpropional, citronellol, eugenol, geraniol, hexyl cinnamal, l-limonene and linalool. The commercially available aerosol antiperspirant product had an average propellant concentration of approximately 85% and an average reservoir pressure of approximately 410 kPA. The commercially available antiperspirant product also had an average total mass flow rate of approximately 1.02 g/sec, and an average antiperspirant composition mass flow rate of approximately 0.20 g/sec.

Forty-eight subjects were enrolled in the study, of which 45 completed the study. The study lasted 26 days, comprising a 21 day washout period in which the subjects used no antiperspirant products (deodorant products only were applied) followed by a 5 day treatment period with the aerosol antiperspirant products. The antiperspirant products were applied once each morning, for 2 seconds from a distance of 6 inches by clinical personnel, during the 5 day treatment period. Hot room evaluations for sweat production were conducted prior to start of the 5 day treatment period (baseline) and 12 hours post the $5^{th}$ day of the treatment period. The adjusted mean sweat values (mg sweat) at the start of the study (baseline) and twelve hours post treatment day 5 are shown in Table 2 below.

TABLE 2

| | Mean Sweat at Baseline (mg of sweat collected) | Baseline Adjusted Mean Sweat Value 12 hrs Post Treatment Day #5 (mg of sweat collected) |
|---|---|---|
| Aerosol Products with Antiperspirant Composition of Example 24 | 595 | 382 |
| Aerosol Products with Antiperspirant Composition of Example 25 | 591 | 362 |
| Aerosol Products with Antiperspirant Composition of Example 26 | 665 | 343 |
| Aerosol Products with Antiperspirant Composition of Comparative Example 27 | 676 | 405 |
| Commercially Available Aerosol Product | 591 | 439 |

After five days of treatment, the aerosol antiperspirant products comprising the antiperspirant compositions of Examples 24, 25 and 26 resulted in lower mean sweat values (mg of sweat) twelve hours post treatment day #5 than both the commercially available antiperspirant product and comparative Example 27. A lower mean sweat value means less perspiration was released from the eccrine glands in the underarm area to the skin surface, and therefore the antiperspirant product had a higher product efficacy. The results for the aerosol products of Examples 25 and 26 were statistically significant (with at least a 90% confidence level). The results for the composition of Example 26 are particularly notable, as this composition had the lowest concentration of antiperspirant active among Examples 24, 25 and 26 and yet had the lowest mean sweat value post treatment among the tested antiperspirant compositions. This may be due to the higher dimethicone concentration, which may have increased substantivity of the antiperspirant active on skin compared to the antiperspirant compositions of Examples 24 and 25. The commercially available product, which had the highest propellant concentration, had the highest mean sweat value post treatment despite having the highest antiperspirant mass flow rate among the products. This may be due, at least in part, to the low antiperspirant composition deposition efficiency of the commercially available product in combination with a lack of antiperspirant active substantivity resulting from the use of a volatile silicone fluid as the liquid carrier. The mean sweat value post treatment for the antiperspirant compositions of Example 25 were directionally better than the value for the compositions of Example 26, possibly due to the hydrophilic tapioca material enabling better antiperspirant active release compared to the hydrophobically modified tapioca material of Example 26. The mean sweat value post treatment for antiperspirant compositions of comparative Example 27 was directionally worse than the value for the antiperspirant compositions of Example 25. This may be due to reduced antiperspirant active substantivity resulting from use of the volatile silicone fluid in comparative Example 27 compared to use of a non-volatile silicone fluid in the antiperspirant compositions of Example 25.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All numeric values (e.g., dimensions, flow rates, pressures, concentrations, etc.) recited herein are modified by the term "about", even if not expressly so stated with the numeric value.

Every document cited herein, including any cross referenced or related patent or application, including without limitation U.S. Ser. No. 61/701,201 filed Sep. 14, 2012, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol antiperspirant composition, comprising:
a liquid propellant having a concentration from 30% to 65% by weight of aerosol antiperspirant composition;
an antiperspirant composition comprising:
one or more liquid materials comprising 70% to 100% by weight of the liquid materials, of non-volatile polydimethyl siloxane fluid; the one or more liquid materials having a concentration from 40% to 70% by weight of the antiperspirant composition;
antiperspirant active particulates;
wherein the antiperspirant composition has a L/P ratio of from about 0.6 to about 1.6, an A/P ratio of from about 0.1 to about 0.95, and a viscosity from 1,000 centipoise to about 50,000 centipoise.

2. The aerosol antiperspirant composition of claim 1, wherein the antiperspirant composition is in the form of a dispersion.

3. An aerosol antiperspirant composition according to claim 1, wherein the one or more liquid materials of the antiperspirant composition consist essentially of non-volatile polydimethyl siloxane fluid, a liquid fragrance material and silicone gum.

4. An aerosol antiperspirant composition according to claim 1, further comprising a particulate fragrance material having a concentration from about 0.25% to about 5% by weight of the antiperspirant composition.

5. An aerosol antiperspirant composition according to claim 1, further comprising a liquid fragrance material having a concentration less than 4% by weight of the antiperspirant composition.

6. An aerosol antiperspirant composition according to claim 1, wherein the non-volatile silicone fluids have a concentration from about 40% to 55% by weight of the antiperspirant composition.

7. An aerosol antiperspirant composition according to claim 1, wherein the antiperspirant composition has a total particulate concentration from 30% to 60% by weight of the antiperspirant composition.

8. An aerosol antiperspirant composition according to claim 1, wherein the antiperspirant composition is substantially or completely free of a silicone gum.

9. An aerosol antiperspirant composition according to claim 1, wherein the L/P ratio is from about 0.6 to about 1.4.

10. An aerosol antiperspirant composition according to claim 1, wherein the non-volatile polydimethyl siloxane fluid consists essentially of a polydimethyl siloxane fluid having a viscosity of 5 centistokes to 350 centistokes.

11. An aerosol antiperspirant composition according to claim 1, wherein the one or more liquid materials comprise less than 10% by weight of volatile silicone fluids.

12. An aerosol antiperspirant composition according to claim 1, wherein the antiperspirant composition is substantially or completely free of volatile silicone fluids.

13. An aerosol antiperspirant composition according to claim 1, wherein the particulates of the antiperspirant active have a concentration less than 34% by weight of the antiperspirant composition.

14. An aerosol antiperspirant composition according to claim 1, further comprising one or more bulking or suspending materials selected from the group consisting of a silica material, a clay material and combinations thereof.

15. An aerosol antiperspirant composition according to claim 1, further comprising one or more non-antiperspirant active particulates selected from the group consisting of particulate fragrance materials, native starches and combinations thereof.

16. An aerosol antiperspirant composition according to claim 1, wherein the antiperspirant composition has a viscosity from 3,000 centipoises to 40,000 centipoises.

17. An aerosol antiperspirant composition according to claim 1, wherein the liquid propellant has a concentration from about 50% to 65% by weight of the aerosol antiperspirant composition.

18. An aerosol antiperspirant composition according to claim 1, wherein the A/P ratio is from 0.3 to 0.75.

19. A product, comprising a reservoir, an actuator comprising a discharge orifice, and a valve in fluid communication with the discharge orifice and the reservoir, the reservoir storing an aerosol antiperspirant composition according to claim 1.

20. A method of using the product of claim 19, wherein the antiperspirant composition is sprayed onto an axillia surface.

* * * * *